United States Patent
Jaiser et al.

(10) Patent No.: US 11,826,586 B2
(45) Date of Patent: Nov. 28, 2023

(54) METHOD FOR DYEING KERATIN MATERIAL, COMPRISING THE USE OF AN ORGANIC $C_1$-$C_6$-ALKOXY-SILANE AND AN ALKALISING AGENT

(71) Applicant: Henkel AG & Co. KGaA, Duesseldorf (DE)

(72) Inventors: Phillip Jaiser, Langenfeld (DE); Torsten Lechner, Langenfeld (DE); Gabriele Weser, Neuss (DE); Marc Nowottny, Moenchengladbach (DE); Carsten Mathiaszyk, Essen (DE); Caroline Kriener, Duesseldorf (DE); Juergen Schoepgens, Schwalmtal (DE); Claudia Kolonko, Remscheid (DE); Ulrike Schumacher, Duesseldorf (DE); Udo Erkens, Willich (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/631,829

(22) PCT Filed: Jun. 8, 2020

(86) PCT No.: PCT/EP2020/065782
§ 371 (c)(1),
(2) Date: Jan. 31, 2022

(87) PCT Pub. No.: WO2021/018444
PCT Pub. Date: Feb. 4, 2021

(65) Prior Publication Data
US 2022/0280816 A1    Sep. 8, 2022

(30) Foreign Application Priority Data
Aug. 1, 2019   (DE) .......................... 102019211505.5

(51) Int. Cl.
| *A61Q 5/10* | (2006.01) |
| *A61Q 5/06* | (2006.01) |
| *A61K 8/02* | (2006.01) |
| *A61K 8/25* | (2006.01) |
| *A61K 8/41* | (2006.01) |
| *A61K 8/44* | (2006.01) |
| *A61K 8/58* | (2006.01) |

(52) U.S. Cl.
CPC ............ *A61Q 5/065* (2013.01); *A61K 8/0258* (2013.01); *A61K 8/25* (2013.01); *A61K 8/41* (2013.01); *A61K 8/44* (2013.01); *A61K 8/585* (2013.01); *A61K 2800/43* (2013.01); *A61K 2800/884* (2013.01)

(58) Field of Classification Search
CPC ........ A61Q 5/065; A61Q 5/10; A61K 8/0258; A61K 8/25; A61K 8/41; A61K 8/44; A61K 8/585; A61K 2800/43; A61K 2800/884
USPC ............................................................. 8/405
See application file for complete search history.

(56) References Cited

U.S. PATENT DOCUMENTS

2010/0083446 A1 *   4/2010   Brun ...................... A61K 8/891
                                                                        8/405

FOREIGN PATENT DOCUMENTS

| DE | 102014222374 A1 | 5/2016 |
| EP | 1767187 A2 | 3/2007 |
| EP | 2168633 A2 | 3/2010 |
| WO | 2013068979 A2 | 5/2013 |
| WO | 2018130912 A1 | 7/2018 |

* cited by examiner

Primary Examiner — Eisa B Elhilo
(74) Attorney, Agent, or Firm — Lorenz & Kopf, LLP

(57) ABSTRACT

An object of the present disclosure is a process for coloring keratinous material, in particular human hair. The process includes applying on the keratinous material a first composition (A). The first composition (A) includes (A1) one or more organic $C_1$-$C_6$ alkoxy silanes and/or condensation products thereof, and (A2) at least one colorant compound selected from the group of pigments and/or direct dyes. The process further includes applying a second composition (B) on the keratinous material. The second composition (B) includes (B1) at least one alkalizing agent.

16 Claims, No Drawings

METHOD FOR DYEING KERATIN MATERIAL, COMPRISING THE USE OF AN ORGANIC $C_1$-$C_6$-ALKOXY-SILANE AND AN ALKALISING AGENT

CROSS-REFERENCE TO RELATED APPLICATION

This application is a U.S. National-Stage entry under 35 U.S.C. § 371 based on International Application No. PCT/EP2020/065782, filed Jun. 8, 2020, which was published under PCT Article 21(2) and which claims priority to German Application No. 102019211505.5, filed Aug. 1, 2019, which are all hereby incorporated in their entirety by reference.

TECHNICAL FIELD

The present application is in the field of cosmetics and concerns a process for coloring keratinous material, in particular human hair, which includes the use of two compositions (A) and (B). Composition (A) is a composition including at least one $C_1$-$C_6$ organic alkoxysilane (A1) and at least one coloring compound (A2), and composition (B) includes at least one alkalizing agent (B1).

A second object of the present disclosure is a multi-component packaging unit (kit-of-parts) for dyeing keratinous material, which includes, separately packaged in two packaging units, the two compositions (A) and (B) described above

Background

The change in shape and color of keratin fibers, especially hair, is a key area of modern cosmetics. To change the hair color, the expert knows various coloring systems depending on coloring requirements. Oxidation dyes are usually used for permanent, intensive dyeing with good fastness properties and good grey coverage. Such dyes usually contain oxidation dye precursors, so-called developer components and coupler components, which form the actual dyes with one another under the influence of oxidizing agents, such as hydrogen peroxide. Oxidation dyes are exemplified by very long-lasting dyeing results.

When direct dyes are used, ready-made dyes diffuse from the colorant into the hair fiber. Compared to oxidative hair dyeing, the dyeing obtained with direct dyes have a shorter shelf life and quicker wash ability. Dyeing with direct dyes usually remain on the hair for a period of between 5 and 20 washes.

The use of color pigments is known for short-term color changes on the hair and/or skin. Color pigments are understood to be insoluble, coloring substances. These are present undissolved in the dye formulation in the form of small particles and are only deposited from the outside on the hair fibers and/or the skin surface. Therefore, they can usually be removed again without residue by a few washes with detergents including surfactants. Various products of this type are available on the market under the name hair mascara.

EP 2168633 B1 deals with the task of producing long-lasting hair colorations using pigments. The paper teaches that when a combination of pigment, organic silicon compound, hydrophobic polymer and a solvent is used on hair, it is possible to produce colorations that are particularly resistant to shampooing.

The organic silicon compounds used in EP 2168633 B1 are reactive compounds from the class of alkoxy silanes. These alkoxy silanes hydrolyze at high rates in the presence of water and form hydrolysis products and/or condensation products, depending on the amounts of alkoxy silane and water used in each case. The influence of the amount of water used in this reaction on the properties of the hydrolysis or condensation product are described, for example, in WO 2013068979 A2.

When these alkoxy silanes or their hydrolysis or condensation products are applied to keratinous material, a film or coating forms on the keratinous material, which completely coats the keratinous material and, in this way, strongly influences the properties of the keratinous material. Areas of application include permanent styling or permanent shape modification of keratin fibers. In this process, the keratin fibers are mechanically shaped into the desired form and then fixed in this form by forming the coating described above. Another particularly suitable application is the coloring of keratin material; in this application, the coating or film is produced in the presence of a coloring compound, for example a pigment. The film colored by the pigment remains on the keratin material or keratin fibers and results in surprisingly wash-resistant colorations.

BRIEF SUMMARY

Processes for dyeing keratinous material, in particular human hair, are provided herein. In an exemplary embodiment, the process includes applying a first composition (A) to the keratinous material. The first composition (A) includes (A1) one or more organic C1-C6 alkoxy silanes and/or condensation products thereof, and (A2) at least one colorant compound selected from the group of pigments, direct dyes, or combinations thereof. The process further includes applying a second composition (B) to the keratinous material. The second composition (B) including (B1) at least one alkalizing agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The great advantage of the alkoxy silane-based dyeing principle is that the high reactivity of this class of compounds enables fast coating. This means that good coloring results can be achieved even after short application periods of just a few minutes. The shorter the exposure times of the hair treatment products, the higher the comfort for the user. However, especially with short application periods, the color intensity of the coloration obtained is still in need of optimization. There is also still room for improvement regarding the durability of the dyeing, especially its wash fastness.

It was the task of the present application to find a process for dyeing keratinous material which shows improvements in terms of color intensity and fastness properties. If a short application period is chosen that is particularly convenient for the user, the color intensity, wash fastness and rub fastness should be improved compared to the colorations that can be achieved so far with the formulations known from the prior art.

Surprisingly, it has been found that this task can be fully solved if the keratin material is dyed in a process in which two compositions (A) and (B) are applied to the keratin material. Here, the first composition (A) includes at least one organic $C_1$-$C_6$ alkoxy silane and/or their condensation product and furthermore at least one color-imparting compound. The second composition (B) is exemplified by its content of at least one alkalizing agent.

A first object of the present disclosure is a method for coloring keratinous material, in particular human hair, wherein on the keratinous material are applied:

a first composition (A) including:
(A1) one or more organic $C_1$-$C_6$ alkoxy silanes and/or condensation products thereof, and
(A2) at least one colorant compound selected from the group of pigments and direct dyes
a second composition (B) including
(B1) at least one alkalizing agent If the composition (A) was applied to the keratin material as part of a dyeing process, an increase in color intensity was observed if the composition (B) was applied to the keratin material in the form of an after treatment agent after application of the composition (A). In addition to the enhancement of color intensity, an improvement in wash fastness and rub fastness was surprisingly also observed in this context.

Treatment of Keratinous Material

Keratinous material includes hair, skin, nails (such as fingernails and/or toenails). Wool, furs and feathers also fall under the definition of keratinous material.

Preferably, keratinous material is understood to be human hair, human skin and human nails, especially fingernails and toenails. Keratinous material is understood to be human hair.

Agents for treating keratinous material are understood to mean, for example, features for coloring the keratinous material, features for reshaping or shaping keratinous material, in particular keratinous fibers, or also features for conditioning or caring for the keratinous material. The agents prepared by the process of the present disclosure are particularly suitable for coloring keratinous material, in particular keratinous fibers, which are preferably human hair.

The term "coloring agent" is used in the context of the present disclosure to refer to a coloring of the keratin material, of the hair, caused using coloring compounds, such as thermochromic and photochromic dyes, pigments, mica, direct dyes. In this staining process, the colorant compounds are deposited in a particularly homogeneous and smooth film on the surface of the keratin material or diffuse into the keratin fiber. The film forms in situ by oligomerization or polymerization of the organic alkoxy silane(s), and by the interaction of the color-imparting compound and organic silicon compound and optionally other ingredients, such as a film-forming, polymer.

Organic $C_1$-$C_6$ Alkoxy Silanes (A1) and/or their Condensation Products in the Composition (A)

The composition (A) is wherein it includes one or more organic $C_1$-$C_6$ alkoxy silanes (A1) and/or their condensation products.

The organic $C_1$-$C_6$ alkoxy silane(s) are organic, non-polymeric silicon compounds, preferably selected from the group of silanes including one, two or three silicon Organic silicon compounds, alternatively called organosilicon compounds, are compounds which either have a direct silicon-carbon bond (Si—C) or in which the carbon is bonded to the silicon atom via an oxygen, nitrogen or sulfur atom. The organic silicon compounds of the present disclosure are preferably compounds including one to three silicon atoms. Organic silicon compounds preferably contain one or two silicon atoms.

According to IUPAC rules, the term silane chemical compounds based on a silicon skeleton and hydrogen. In organic silanes, the hydrogen atoms are completely or partially replaced by organic groups such as (substituted) alkyl groups and/or alkoxy groups.

A characteristic feature of the $C_1$-$C_6$ alkoxy silanes of the present disclosure is that at least one $C_1$-$C_6$ alkoxy group is directly bonded to a silicon atom. The $C_1$-$C_6$ alkoxy silanes as contemplated herein thus include at least one structural unit R'R"R'''Si—O—($C_1$-$C_6$ alkyl) where the radicals R', R" and R''' stand for the three remaining bond valencies of the silicon atom.

The $C_1$-$C_6$ alkoxy group or groups bonded to the silicon atom are very reactive and are hydrolyzed at high rates in the presence of water, the reaction rate depending, among other things, on the number of hydrolysable groups per molecule. If the hydrolysable $C_1$-$C_6$ alkoxy group is an ethoxy group, the organic silicon compound preferably includes a structural unit R'R"R'''Si—O—$CH_2$—$CH_3$. The R', R" and R''' residues again represent the three remaining free valences of the silicon atom.

Even the addition of insignificant amounts of water leads first to hydrolysis and then to a condensation reaction between the organic alkoxy silanes. For this reason, both the organic alkoxy silanes (A1) and their condensation products may be present in the composition.

A condensation product is understood to be a product formed by reaction of at least two organic $C_1$-$C_6$ alkoxy silanes with elimination of water and/or with elimination of a $C_1$-$C_6$ alkanol.

The condensation products can, for example, be dimers, or even trimers or oligomers, where in the condensation products are always in balance with the monomers.

Depending on the amount of water used or consumed in the hydrolysis, the equilibrium shifts from monomeric $C_1$-$C_6$ alkoxysilane to condensation product.

In a very particularly preferred embodiment, a process as contemplated herein is wherein the composition (A) includes one or more organic $C_1$-$C_6$ alkoxy silanes (A1) selected from silanes having one, two or three silicon atoms, the organic silicon compound further including one or more basic chemical functions.

This basic group can be, for example, an amino group, an alkylamino group or a dialkylamino group, which is preferably connected to a silicon atom via a linker. Preferably, the basic group is an amino group, a $C_1$-$C_6$ alkylamino group or a di($C_1$-$C_6$)alkylamino group.

A very particularly preferred method as contemplated herein is wherein the composition (A) includes one or more organic $C_1$-$C_6$ alkoxy silanes (A1) selected from the group of silanes having one, two or three silicon atoms, and wherein the $C_1$-$C_6$ alkoxy silanes further include one or more basic chemical functions.

Particularly satisfactory results were obtained when $C_1$-$C_6$ alkoxy silanes of the formula (S-I) and/or (S-II) were used in the process as contemplated herein. Since, as previously described, hydrolysis/condensation already starts at traces of moisture, the condensation products of the $C_1$-$C_6$ alkoxy silanes of formula (S-I) and/or (S-II) are also included in this embodiment.

In another very particularly preferred embodiment, a process as contemplated herein is wherein the first composition (A) includes one or more organic $C_1$-$C_6$ alkoxy silanes (A1) of the formula (S-I) and/or (S-II), $$R_1R_2N\text{---}L\text{---}Si(OR_3)_a(R_4)_b \qquad (S\text{-}I)$$

where
$R_1$, $R_2$ independently represent a hydrogen atom or a $C_1$-$C_6$ alkyl group,
L is a linear or branched divalent $C_1$-$C_{20}$ alkylene group,
$R_3$, $R_4$ independently of one another represent a $C_1$-$C_6$ alkyl group,
a, stands for an integer from 1 to 3, and
b stands for the integer 3-a, and $$(R_5O)_c(R_6)_dSi\text{---}(A)_e\text{---}[NR_7\text{-}(A')]_f\text{---}[O\text{---}(A'')]_g\text{---}[NR_8\text{-}(A''')]_h\text{---}Si(R_6')_{d'}(OR_5')_{c'} \qquad (S\text{-}II),$$

where
R5, R5', R5", R6, R6' and R6" independently represent a $C_1$-$C_6$ alkyl group,
A, A', A", A''' and A'''' independently represent a linear or branched divalent $C_1$-$C_{20}$ alkylene group,
$R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (S-III), $$(A'''')\text{---}Si(R_6'')_{d''}(OR_5'')_{c''} \qquad (S\text{-}III),$$

c, stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
provided that at least one of e, f, g and h is different from 0, and/or their condensation products.

The substituents $R_1$, $R_2$, $R_3$, $R_4$, $R_5$, $R_5'$, $R_5''$, $R_6$, $R_6'$, $R_6''$, $R_7$, $R_8$, L, A, A', A", A''' and A'''' in the compounds of formula (S-I) and (S-II) are explained below as examples: Examples of a $C_1$-$C_6$ alkyl group are the groups methyl, ethyl, propyl, isopropyl, n-butyl, s-butyl and t-butyl, n-pentyl and n-hexyl. Propyl, ethyl and methyl are preferred alkyl radicals. Examples of a $C_2$-$C_6$ alkenyl group are vinyl, allyl, but-2-enyl, but-3-enyl and isobutenyl, preferred $C_2$-$C_6$ alkenyl radicals are vinyl and allyl. Preferred examples of a hydroxy $C_1$-$C_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino $C_1$-$C_6$ alkyl group are the aminomethyl group, the 2-aminoethyl group, the 3-aminopropyl group. The 2-aminoethyl group is particularly preferred. Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—$CH(CH_3)$—) and (—$CH_2$—$CH(CH_3)$—$CH_2$—).

In the organic silicon compounds of the formula (S-I)

$$R_1R_2N\text{---}L\text{---}Si(OR_3)_a(R_4)_b \qquad (S\text{-}I)$$

the radicals $R_1$ and $R_2$ independently of one another represent a hydrogen atom or a $C_1$-$C_6$ alkyl group. Very preferably, $R_1$ and $R_2$ both represent a hydrogen atom.

In the middle part of the organic silicon compound is the structural unit or the linker -L- which stands for a linear or branched, divalent $C_1$-$C_{20}$ alkylene group. The divalent $C_1$-$C_{20}$ alkylene group may alternatively be referred to as a divalent or divalent $C_1$-$C_{20}$ alkylene group, by which is meant that each—L grouping may form—two bonds.

Preferably —L— stands for a linear, bivalent $C_1$-$C_{20}$ alkylene group. Further preferably —L— stands for a linear bivalent $C_1$-$C_6$ alkylene group. Particularly preferred —L stands for a methylene group (—$CH_2$—), an ethylene group (—$CH_2$—$CH_2$—), propylene group (—$CH_2$—$CH_2$—$CH_2$—) or butylene (—$CH_2$—$CH_2$—$CH_2$—$CH_2$—). L stands for a propylene group (—$CH_2$—$CH_2$—$CH_2$—)

The organic silicon compounds of formula (S-I) as contemplated herein.

$$R_1R_2N\text{---}L\text{---}Si(OR_3)_a(R_4)_b (S\text{-}I),$$

one end of each carries the silicon-including group —$Si(OR_3)_a(R_4)_b$.

In the terminal structural unit —$Si(OR_3)_a(R_4)_b$, the radicals $R_3$ and $R_4$ independently represent a $C_1$-$C_6$ alkyl group, and in particular preferably $R_3$ and $R_4$ independently represent a methyl group or an ethyl group.

Here a stands for an integer from 1 to 3, and b stands for the integer 3-a. If a stands for the number 3, then b is equal to 0. If a stands for the number 2, then b is equal to 1. If a stands for the number 1, then b is equal to 2.

Keratin treatment agents with particularly suitable properties could be prepared if the composition (A) includes at least one organic $C_1$-$C_6$ alkoxy silane of the formula (S-I) in which the radicals $R_3$, $R_4$ independently of one another represent a methyl group or an ethyl group.

Furthermore, dyeing with the best wash fastness could be obtained if the composition (A) includes at least one organic $C_1$-$C_6$ alkoxy silane of the formula (S-I) in which the radical a represents the number 3. In this case the radical b stands for the number 0.

In a further preferred embodiment, a process as contemplated herein is wherein the composition (A) includes one or more organic $C_1$-$C_6$ alkoxy silanes of the formula (S-I), where
$R_3$, $R_4$ independently of one another represent a methyl group or an ethyl group and
a stands for the number 3 and
b stands for the number 0.

In a further preferred embodiment, a process as contemplated herein is wherein the composition (A) includes at least one or more organic $C_1$-$C_6$ alkoxy silanes of the formula (S-I), $$R_1R_2N\text{---}L\text{---}Si(OR_3)_a(R_4)_b \qquad (S\text{-}I),$$

where
$R_1$, $R_2$ both represent a hydrogen atom, and
L represents a linear, bivalent $C_1$-$C_6$-alkylene group, preferably a propylene group (—$CH_2$—$CH_2$—$CH_2$—) or an ethylene group (—$CH_2$—$CH_2$—),
$R_3$ represents an ethyl group or a methyl group,
$R_4$ represents a methyl group or an ethyl group,
a stands for the number 3 and
b stands for the number 0.

Organic silicon compounds of the formula (I) which are particularly suitable for solving the problem as contemplated herein are (3-Aminopropyl)triethoxysilane

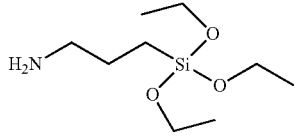

(3-Aminopropyl)trimethoxysilane

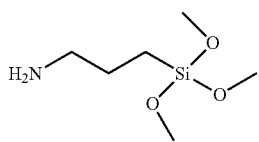

(2-Aminoethyl)triethoxysilane

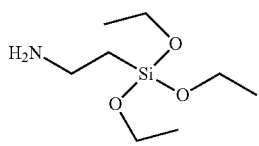

(2-Aminoethyl)trimethoxysilane

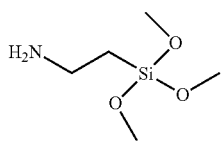

(3-Dimethylaminopropyl)trimethoxysilane

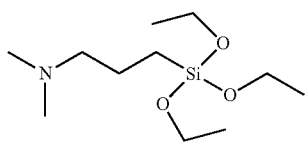 [SMILES: CCO[Si](CCCN(C)C)(OCC)OCC]

(3-Dimethylaminopropyl)trimethoxysilane

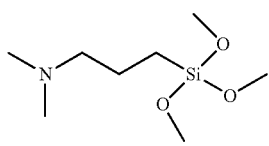

(2-Dimethylaminoethyl)triethoxysilane.

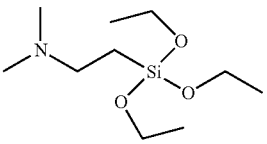

(2-Dimethylaminoethyl)trimethoxysilane and/or

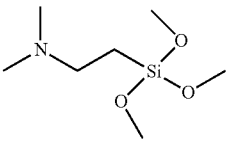

In a further preferred embodiment, a process as contemplated herein is wherein the first composition (A) includes at least one organic $C_1$-$C_6$ alkoxysilane (A1) of formula (S-I) selected from the group of
(3-Aminopropyl)triethoxysilane
(3-Aminopropyl)trimethoxysilane
(2-Aminoethyl)triethoxysilane
(2-Aminoethyl)trimethoxysilane
(3-Dimethylaminopropyl)triethoxysilane
(3-Dimethylaminopropyl)trimethoxysilane
(2-Dimethylaminoethyl)triethoxysilane,
(2-Dimethylaminoethyl)trimethoxysilane and/or their condensation products.

The organic silicon compound of formula (I) is commercially available. (3-aminopropyl)trimethoxysilane, for example, can be purchased from Sigma-Aldrich. Also (3-aminopropyl)triethoxysilane is commercially available from Sigma-Aldrich.

In a further embodiment of the process as contemplated herein, composition (A) may also include one or more organic $C_1$-$C_6$ alkoxy silanes of formula (S-II), $$(R_5O)_c(R_6)_dSi—(A)_e-[NR_7—(A')]_f-[O—(A'')]_g-[NR_8-(A''')]_h—Si(R_6')_{d'}(OR_5')_{c'} \quad \text{(S-II)}.$$

The organosilicon compounds of the formula (S-II) as contemplated herein each carry at their two ends the silicon-including groupings $(R_5O)_c(R_6)_dSi—$ and $—Si(R_6')_{d'}(OR_5')_{c'}$.

In the central part of the molecule of formula (S-II) there are the groups $—(A)_e—$ and $-[NR_7—(A')]_f-$ and $-[O—(A'')]_g-$ and $-[NR_8-(A''')]_h-$. Here, each of the radicals e, f, g and h can independently of one another stand for the number 0 or 1, with the proviso that at least one of the radicals e, f, g and h is different from 0. In other words, an organic silicon compound of formula (II) as contemplated herein includes at least one grouping from the group including $-(A)—$ and $—[NR_7—(A')]—$ and $—[O—(A'')]—$ and $—[NR_8-(A''')]—$.

In the two terminal structural units $(R_5O)_c(R_6)_dSi—$ and $—Si(R_6')_{d'}(OR_5')_{c'}$, the residues $R_5$, $R_5'$, $R_5''$ independently represent a $C_1$-$C_6$ alkyl group. The radicals $R_6$, $R_6'$ and $R_6''$ independently represent a $C_1$-$C_6$ alkyl group.

Here a stands for an integer from 1 to 3, and d stands for the integer 3-c. If c stands for the number 3, then d is equal to 0. If c stands for the number 2, then d is equal to 1. If c stands for the number 1, then d is equal to 2.

Analogously c' stands for a whole number from 1 to 3, and d' stands for the whole number 3-c'. If c' stands for the number 3, then d' is 0. If c' stands for the number 2, then d' is 1. If c' stands for the number 1, then d' is 2.

Dyeing with the best wash fastness values could be obtained if the residues c and c' both stand for the number 3. In this case d and d' both stand for the number 0.

In a further preferred embodiment, a process as contemplated herein is wherein the composition (A) includes one or more organic $C_1$-$C_6$ alkoxy silanes of the formula (S- II),

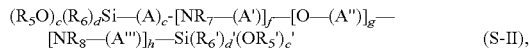
$$(R_5O)_c(R_6)_dSi-(A)_e-[NR_7-(A')]_f-[O-(A'')]_g-[NR_8-(A''')]_h-Si(R_6')_{d'}(OR_5')_{c'}' \quad \text{(S-II)},$$

where
$R_5$ and $R_5'$ independently represent a methyl group or an ethyl group,
c and c' both stand for the number 3 and
d and d' both stand for the number 0.

When c and c' are both 3 and d and d' are both 0, the organic silicon compounds as contemplated herein correspond to the formula (S-IIa)

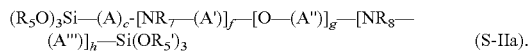
$$(R_5O)_3Si-(A)_e-[NR_7-(A')]_f-[O-(A'')]_g-[NR_8-(A''')]_h-Si(OR_5')_3 \quad \text{(S-IIa)}.$$

The radicals e, f, g and h can independently stand for the number 0 or 1, whereby at least one radical from e, f, g and h is different from zero. The abbreviations e, f, g and h thus define which of the groupings -(A)$_e$-and —[NR$_7$—(A')]$_f$— and —[O—(A'')]$_g$—and —[NR$_8$—(A''')]$_h$—are in the middle part of the organic silicon compound of formula (II).

In this context, the presence of certain groupings has proven to be particularly advantageous in terms of achieving washfast dyeing results. Particularly satisfactory results could be obtained if at least two of the radicals e, f, g and h stand for the number 1. Especially preferred e and f both stand for the number 1. Furthermore, g and h both stand for the number 0.

When e and f are both 1 and g and h are both 0, the organic silicon compounds as contemplated herein are represented by the formula (S-IIb)

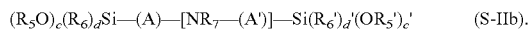
$$(R_5O)_c(R_6)_dSi-(A)-[NR_7-(A')]-Si(R_6')_{d'}(OR_5')_{c'}' \quad \text{(S-IIb)}.$$

The radicals A, A', A", A''' and A" " independently represent a linear or divalent, bivalent $C_1$-$C_{20}$ alkylene group. Preferably the radicals A, A', A", A''' and A" " independently of one another represent a linear, bivalent $C_1$-$C_{20}$ alkylene group. Further preferably the radicals A, A', A", A''' and A" " independently represent a linear bivalent $C_1$-$C_6$ alkylene group.

The divalent $C_1$-$C_{20}$ alkylene group may alternatively be referred to as a divalent or divalent $C_1$-$C_{20}$ alkylene group, by which is meant that each grouping A, A', A", A''' and A" " may form two bonds.

In particular, the radicals A, A', A", A''' and A" " independently of one another represent a methylene group (—CH$_2$—), an ethylene group (—CH$_2$—CH$_2$—), a propylene group (—CH$_2$—CH$_2$—CH$_2$—) or a butylene group (—CH$_2$—CH$_2$—CH$_2$—CH$_2$—). Very preferably, the radicals A, A', A", A''' and A" " represent a propylene group (—CH$_2$—CH$_2$—CH$_2$—).

If the radical f represents the number 1, then the organic silicon compound of formula (II) as contemplated herein includes a structural grouping —[NR$_7$—(A')]—. If the radical f represents the number 1, then the organic silicon compound of formula (II) as contemplated herein includes a structural grouping —[NR$_8$—(A''')]—.

Wherein $R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of the formula (S- III)

$$-(A'''')-Si(R_6'')_{a''}(OR_5'')_{c''} \quad \text{(S-III)}.$$

Very preferably the radicals $R_7$ and $R_8$ independently of one another represent a hydrogen atom, a methyl group, a 2-hydroxyethyl group, a 2-alkenyl group, a 2-aminoethyl group or a grouping of the formula (S- III).

If the radical f represents the number 1 and the radical h represents the number 0, the organic silicon compound as contemplated herein includes the grouping [NR$_7$—(A')] but not the grouping —[NR$_8$—(A''')]. If the radical $R_7$ now stands for a grouping of the formula (III), the organic silicone compound includes 3 reactive silane groups.

In a further preferred embodiment, a process as contemplated herein is wherein the composition (A) includes one or more organic $C_1$-$C_6$ alkoxy silanes (A1) of the formula (S- II),

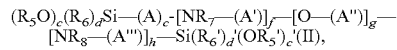
$$(R_5O)_c(R_6)_dSi-(A)_e-[NR_7-(A')]_f-[O-(A'')]_g-[NR_8-(A''')]_h-Si(R_6')_{d'}(OR_5')_{c'}'(II),$$

where
e and f both stand for the number 1,
g and h both stand for the number 0,
A and A' independently represent a linear, divalent $C_1$-$C_6$ alkylene group and
$R_7$ represents a hydrogen atom, a methyl group, a 2-hydroxyethyl group, a 2-alkenyl group, a 2-aminoethyl group or a group of formula (S- III).

In a further preferred embodiment, a process as contemplated herein is wherein the composition (A) includes one or more organic $C_1$-$C_6$ alkoxy silanes (A1) of the formula (S- II), where
e and f both stand for the number 1,
g and h both stand for the number 0,
A and A' independently of one another represent a methylene group(—CH$_2$—), an ethylene group (—CH$_2$—CH$_2$—) or a propylene group (—CH$_2$—CH$_2$—CH$_2$—), and
$R_7$ represents a hydrogen atom, a methyl group, a 2-hydroxyethyl group, a 2-alkenyl group, a 2-aminoethyl group or a group of formula (S- III).

Organic silicon compounds of the formula (S- II) which are well suited for solving the problem as contemplated herein are
—3-(Trimethoxysilyl)-N-[3-(trimethoxysilyl)propyl]—1-propanamine

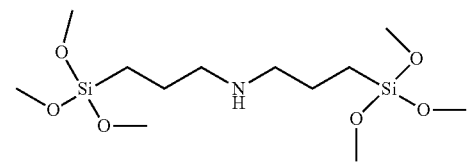

3-(Triethoxysilyl)-N-[3-(triethoxysilyl) propyl]—1-propanamine

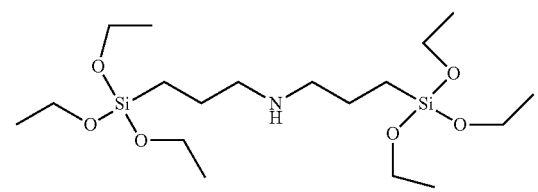 [SMILES: CCO[Si](CCCNCCC[Si](OCC)(OCC)OCC)(OCC)OCC]

N-methyl-3-(trimethoxysilyl)-N-[3-(trimethoxysilyl)propyl]—1-propanamine

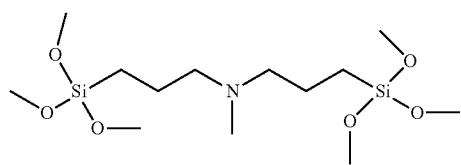

N-Methyl-3-(triethoxysilyl)-N-[3-(triethoxysilyl)propyl]—1-propanamine

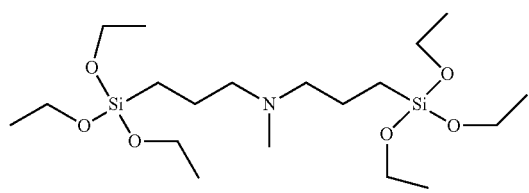 [SMILES: CCO[Si](CCCN(C)CCC[Si](OCC)(OCC)OCC)(OCC)OCC]

2—[Bis[3-(trimethoxysilyl)propyl]amino]-ethanol

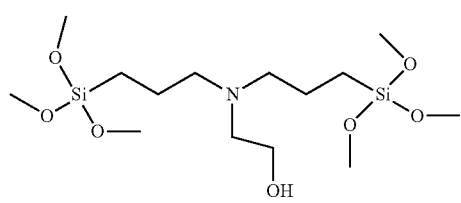

2-[Bis[3-(triethoxysilyl)propyl]amino]ethanol

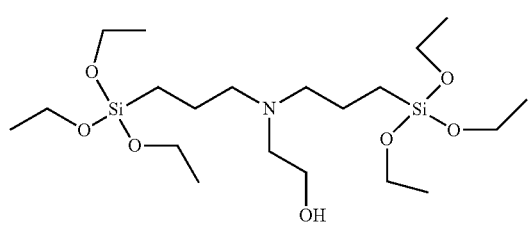 [SMILES: CCO[Si](CCCN(CCO)CCC[Si](OCC)(OCC)OCC)(OCC)OCC]

3-(Trimethoxysilyl)-N,N-bis[3-(trimethoxysilyl)propyl]—1-propanamine

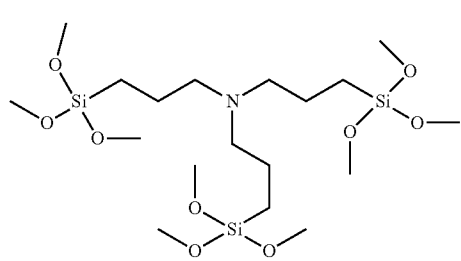

3-(Triethoxysilyl)-N,N-bis[3-(triethoxysilyl)propyl]—1-propanamine

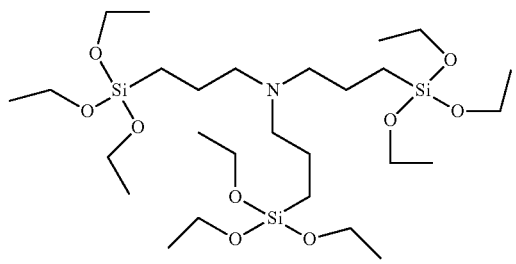 [SMILES: CCO[Si](CCCN(CCC[Si](OCC)(OCC)OCC)CCC[Si](OCC)(OCC)OCC)(OCC)OCC]

N1,N1-Bis[3-(trimethoxysilyl)propyl]—1,2-ethanediamine,

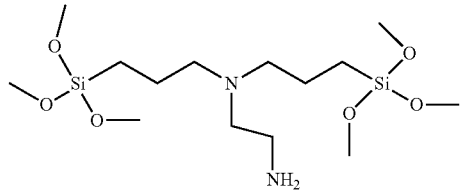

N1,N1-Bis[3-(triethoxysilyl1)propyl1]—1,2-ethanediamine,

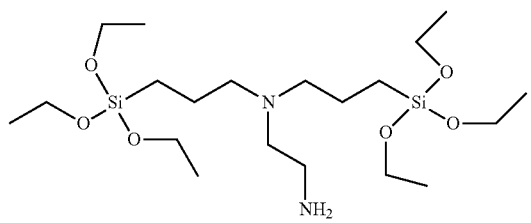 [SMILES: CCO[Si](CCCN(CCN)CCC[Si](OCC)(OCC)OCC)(OCC)OCC]

N,N-Bis[3-(trimethoxysilyl)propyl]—2-propene-1-amine

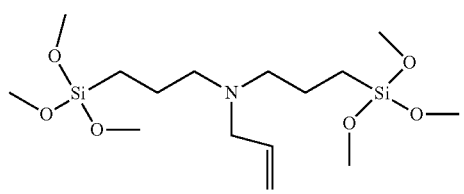

N,N-Bis[3-(triethoxysilyl)propyl]—2-propene-1-amine

The organic silicon compounds of formula (S-II) are commercially available.

Bis(trimethoxysilylpropyl)amines with the CAS number 82985-35-1 can be purchased from Sigma-Aldrich.
Bis[3-(triethoxysilyl)propyl]amines with the CAS number 13497-18-2 can be purchased from Sigma-Aldrich, for example.
N-methyl-3-(trimethoxysilyl)-N-[3-(trimethoxysilyl)propyl]—1-propanamine is alternatively referred to as Bis(3-trimethoxysilylpropyl)-N-methylamine and can be purchased commercially from Sigma-Aldrich or Fluorochem.
3-(triethoxysilyl)-N,N-bis[3-(triethoxysilyl)propyl]—1-propanamine with the CAS number 18784-74-2 can be purchased for example from Fluorochem or Sigma-Aldrich.

In a further preferred embodiment, a process as contemplated herein is wherein the composition (A) includes one or more organic $C_1$-$C_6$ alkoxy silanes of formula (S-II) selected from the group of
3-(Trimethoxysilyl)-N-[3-(trimethoxysilyl)propyl]—1-propanamine
3-(Triethoxysilyl)-N-[3-(triethoxysilyl) propyl]—1-propanamine
N-Methyl-3-(trimethoxysilyl)-N-[3-(trimethoxysilyl)propyl]—1-propanamine
N-Methyl-3-(triethoxysilyl)-N-[3-(triethoxysilyl) propyl]—1-propanamine
2-[Bis[3-(trimethoxysilyl) propyl]amino]-ethanol
2-[Bis[3-(triethoxysilyl) propyl]amino]ethanol
3-(Trimethoxysilyl)-N,N-bis[3-(trimethoxysilyl) propyl]—1-propanamine
3-(Triethoxysilyl)-N,N-bis[3-(triethoxysilyl) propyl]—1-propanamine
N1,N1-Bis[3-(trimethoxysilyl) propyl]—1,2-ethanediamine,
N1,N1-Bis[3-(triethoxysilyl) propyl]—1,2-ethanediamine,
N,N-Bis[3-(trimethoxysilyl)propyl]—2-Propen-1-amine and/or
N,N-Bis[3-(triethoxysilyl)propyl]—2-propen-1-amine, and/or their condensation products.

In further dyeing trials, it has also been found to be particularly advantageous if at least one organic $C_1$-$C_6$ alkoxy silane (A1) of the formula (S-IV) was used in the process as contemplated herein $$R_9Si(OR_{10})_k(R_{11})_m \quad \text{(S-IV)}.$$

The compounds of formula (S-IV) are organic silicon compounds selected from silanes having one, two or three silicon atoms, wherein the organic silicon compound includes one or more hydrolysable groups per molecule.

The organic silicon compound(s) of formula (S-IV) may also be referred to as silanes of the alkyl-$C_1$-$C_6$-alkoxy-silane type, $$R_9Si(OR_{10})_k(R_{11})_m \quad \text{(S-IV)},$$

where
$R_9$ represents a $C_1$-$C_{12}$ alkyl group,
$R_{10}$ represents a $C_1$-$C_6$ alkyl group,
$R_1$ represents a $C_1$-$C_6$ alkyl group
k is an integer from 1 to 3, and
m stands for the integer 3-k.

In a further embodiment, a particularly preferred method as contemplated herein is to
wherein the first composition (A) includes one or more organic $C_1$-$C_6$ alkoxy silanes (A1) of the formula (S-IV), $$R_9Si(OR_{10})_k(R_{10})_m \quad \text{(S-IV)},$$

where
$R_9$ represents a $C_1$-$C_{12}$ alkyl group,
$R_{10}$ represents a $C_1$-$C_6$ alkyl group,
$R_1$ represents a $C_1$-$C_6$ alkyl group
k is an integer from 1 to 3, and
m stands for the integer 3-k, and/or their condensation products.

In the organic $C_1$-$C_6$ alkoxy silanes of formula (S-IV), the $R_9$ radical represents a $C_1$-$C_{12}$ alkyl group. This $C_1$-$C_{12}$ alkyl group is saturated and can be linear or branched. Preferably, $R_9$ represents a linear $C_1$-$C_8$ alkyl group. Preferably $R_9$ stands for a methyl group, an ethyl group, an n-propyl group, an n-butyl group, an n-pentyl group, an n-hexyl group, an n-octyl group or an n-dodecyl group. Particularly preferred, $R_9$ stands for a methyl group, an ethyl group or an n-octyl group.

In the organic silicon compounds of formula (S-IV), the radical $R_{10}$ represents a $C_1$-$C_6$ alkyl group. Highly preferred $R_{10}$ stands for a methyl group or an ethyl group.

In the organic silicon compounds of formula (S-IV), the radical $R_1$ represents a $C_1$-$C_6$ alkyl group. Particularly preferably, $R_{11}$ represents a methyl group or an ethyl group.

Furthermore, k stands for a whole number from 1 to 3, and m stands for the whole number 3-k. If k stands for the number 3, then m is equal to 0. If k stands for the number 2, then m is equal to 1. If k stands for the number 1, then m is equal to 2.

Dyeing with the best wash fastness can be obtained when the composition (A) includes at least one organic $C_1$-$C_6$ alkoxy silane (A1) of formula (S-IV) in which the radical k represents the number 3. In this case the radical m stands for the number 0.

Organic silicum compounds of the formula (S-IV) which are particularly suitable for solving the problem as contemplated herein are Methyltrimethoxysilane

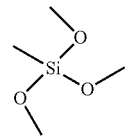

Methyltriethoxysilane

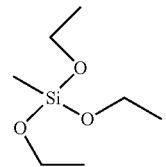

Ethyltrimethoxysilane

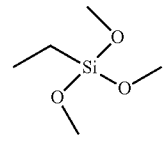

Ethyltriethoxysilane

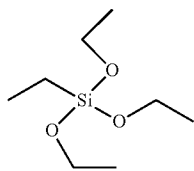

n-Propyltrimethoxysilane (also known as propyltrimethoxysilane)

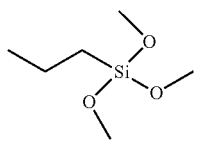

n-Propyltriethoxysilane (also known as propyltriethoxysilane)

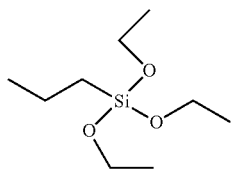

n-Hexyltrimethoxysilane (also known as hexyltrimethoxysilane)

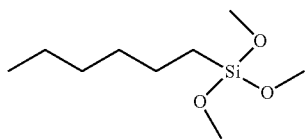

n-Hexyltriethoxysilane (also known as hexyltriethoxysilane)

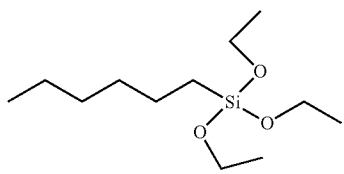 [SMILES: CCCCCC[Si](OCC)(OCC)OCC]

n-Octyltrimethoxysilane (also known as octyltrimethoxysilane)

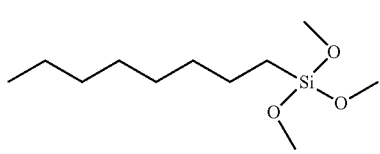

n-Octyltriethoxysilane (also known as octyltriethoxysilane)

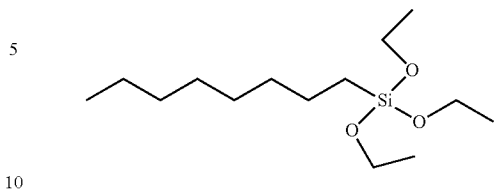

n-Dodecyltrimethoxysilane (also referred to as dodecyltrimethoxysilane) and/or

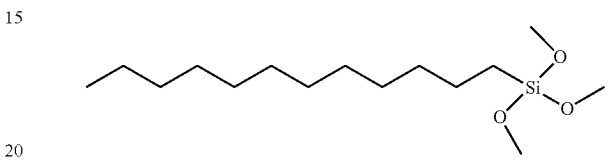

n-Dodecyltriethoxysilane (also referred to as dodecyltriethoxysilane).

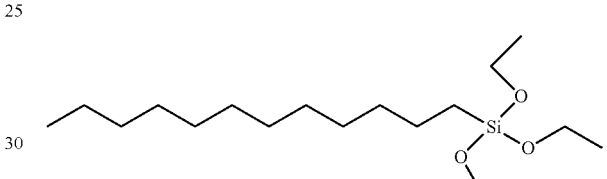

In a further preferred embodiment, a process as contemplated herein is wherein the first composition (A) includes at least one organic $C_1$-$C_6$ alkoxysilane (A1) of formula (S-IV) selected from the group of Methyltrimethoxysilane
Methyltriethoxysilane
Ethyltrimethoxysilane
Ethyltriethoxysilane
Hexyltrimethoxysilane
Hexyltriethoxysilane
Octyltrimethoxysilane
Octyltriethoxysilane
Dodecyltrimethoxysilane,
Dodecyltriethoxysilane, and/or their condensation products.

The corresponding hydrolysis or condensation products are, for example, the following compounds:

Hydrolysis of $C_1$-$C_6$ alkoxy silane of the formula (S-I) with water (reaction scheme using the example of 3-aminopropyltriethoxysilane):

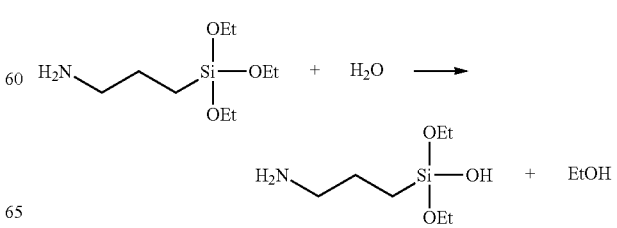

Depending on the amount of water used, the hydrolysis reaction can also take place several times per $C_1$-$C_6$ alkoxy silane used:

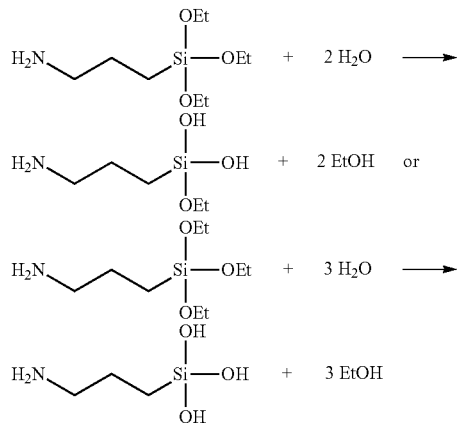

Hydrolysis of $C_1$-$C_6$ alkoxy silane of formula (S-IV) with water (reaction scheme using methyltrimethoxysilane as an example):

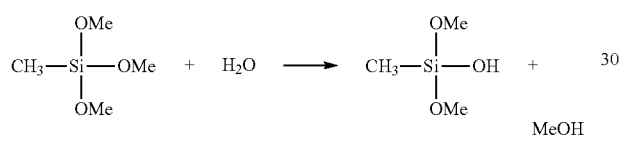

Depending on the amount of water used, the hydrolysis reaction can also take place several times per $C_1$-$C_6$ alkoxy silane used:

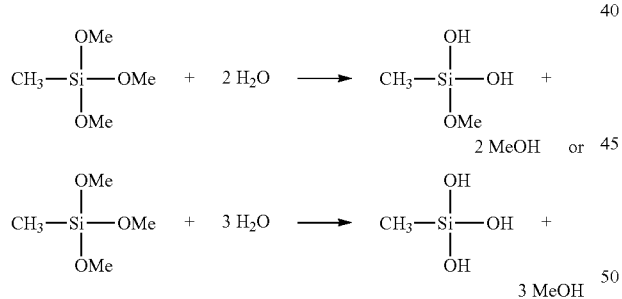

Condensation reactions include (shown using the mixture (3-aminopropyl)triethoxysilane and methyltrimethoxysilane):

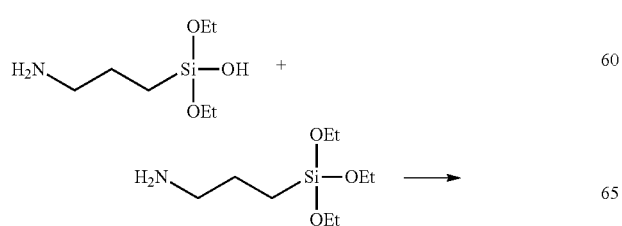

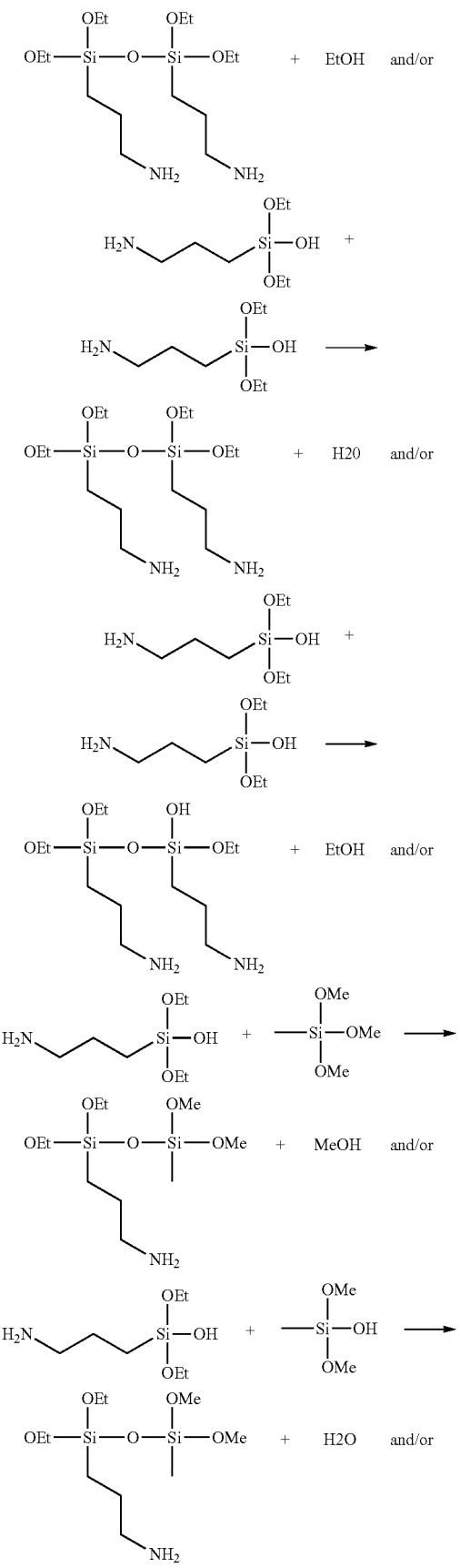

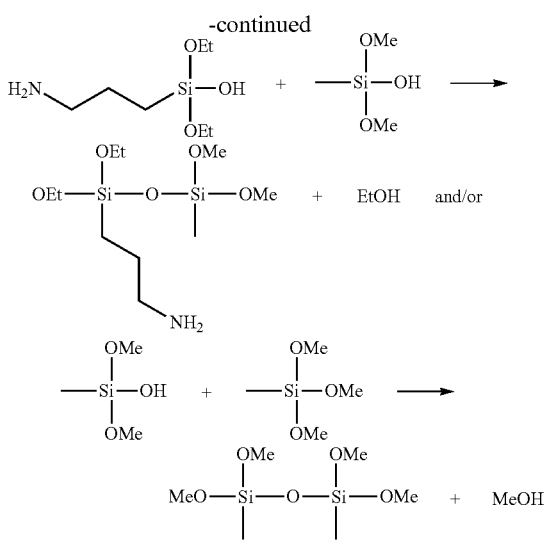

In the above exemplary reaction schemes the condensation to a dimer is shown in each case, but further condensations to oligomers with several silane atoms are also possible and preferred.

Both partially hydrolyzed and fully hydrolyzed $C_1$-$C_6$ alkoxysilanes of the formula (S-I) can participate in these condensation reactions, which undergo condensation with yet unreacted, partially or also fully hydrolyzed $C_1$-$C_6$ alkoxysilanes of the formula (S-I). In this case, the $C_1$-$C_6$ alkoxysilanes of formula (S-I) react with themselves.

Furthermore, both partially hydrolyzed and fully hydrolyzed $C_1$-$C_6$-alkoxysilanes of the formula (S-I) can also participate in the condensation reactions, which undergo condensation with not yet reacted, partially or also fully hydrolyzed $C_1$-$C_6$-alkoxysilanes of the formula (S-IV). In this case, the $C_1$-$C_6$ alkoxysilanes of formula (S-I) react with the $C_1$-$C_6$ alkoxysilanes of formula (S-IV).

Furthermore, both partially hydrolyzed and fully hydrolyzed $C_1$-$C_6$-alkoxysilanes of the formula (S-IV) can also participate in the condensation reactions, which undergo condensation with not yet reacted, partially or also fully hydrolyzed $C_1$-$C_6$-alkoxysilanes of the formula (S-IV). In this case, the $C_1$-$C_6$ alkoxysilanes of formula (S- IV) react with themselves.

The composition (A) as contemplated herein may contain one or more organic $C_1$-$C_6$ alkoxysilanes (A1) in various proportions. The skilled person determines this depending on the desired thickness of the silane coating on the keratin material and on the amount of keratin material to be treated.

Particularly storage-stable preparations with very good dyeing results in application could be obtained when the composition (A) includes—based on its total weight—one or more organic $C_1$-$C_6$-alkoxysilanes (A1) and/or the condensation products thereof in a total amount of from about 30.0 to about 85.0% by weight, preferably from about 35.0 to about 80.0% by weight, more preferably from about 40.0 to about 75.0% by weight, still more preferably from about 45.0 to about 70.0% by weight, and most preferably from about 50.0 to about 65.0% by weight.

In a further embodiment, a much preferred method is wherein the first composition (A)—based on the total weight of the composition (A)-includes one or more organic $C_1$-$C_6$-alkoxysilanes (A2) and/or the condensation products of the total amount of from about 30.0 to about 85.0% by weight, preferably from about 35.0 to about 80.0% by weight, more preferably from about 40.0 to about 75.0% by weight, still more preferably from about 45.0 to about 70.0% by weight, and most preferably from about 50.0 to about 65.0% by weight.

Coloring Compounds (A2) in the Composition (A)

As a second constituent essential to the present disclosure, the composition (A) includes at least one colorant compound (A2) selected from the group of pigments and direct dyes.

As contemplated herein, the colorant compound(s) will be selected from pigments, direct dyes, where direct dyes may also be photochromic dyes and thermochromic dyes.

Very preferably, the composition (A) includes at least one pigment.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, a composition as contemplated herein is wherein it includes at least one colorant compound selected from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-comprising silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, C177510) and/or carmine (cochineal).

Colored pearlescent pigments are also particularly preferred colorants from the group of pigments as contemplated herein. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, muscovite or phlogopite, is coated with a metal oxide.

In the context of a very particularly preferred embodiment, a process as contemplated herein is wherein the first composition (A) includes at least one inorganic pigment (A2) which is preferably selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, the composition (A) as contemplated herein is wherein it includes at least one colorant compound from the group of pigments selected from the group of colored metal oxides, metal hydroxides, metal oxide hydrates, silicates, metal sulfides, complex metal cyanides, metal sulfates, bronze pigments and/or from mica- or mica-based colorant compounds coated with at least one metal oxide and/or a metal oxychloride.

In a further preferred embodiment, a composition (A) as contemplated herein is wherein it includes at least one colorant compound selected from mica- or mica-based pigments reacted with one or more metal oxides selected from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:
Colorona Copper, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491(Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491(Iron oxides)
Colorona Blackstar Gold, Merck, MICA, CI 77499 (IRON OXIDES)
Other particularly preferred color pigments with the trade name Xirona® are for example:
Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.
In addition, particularly preferred color pigments with the trade name Unipure® are for example:
Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica In a further embodiment, composition (A) may also include one or more colorant compounds selected from the group of organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolo-pyrrole, indigo, thioindido, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, a process as contemplated herein is wherein the first composition (A) includes at least one organic pigment (A2) which is preferably selected from the group of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles including a layer of absorbed dyes, the unit of particle and dye being insoluble under the above mentioned conditions. The particles can, for example, be inorganic substrates, which can be aluminum, silica, calcium borosilate, calcium aluminum borosilicate or even aluminum.

For example, alizarin color varnish can be used.

Due to their excellent resistance to light and temperature, the use of the pigments in the means as contemplated herein is particularly preferred. It is also preferred if the pigments used have a certain particle size. This particle size leads on the one hand to an even distribution of the pigments in the formed polymer film and on the other hand avoids a rough hair or skin feeling after application of the cosmetic product. As contemplated herein, it is therefore advantageous if the at least one pigment has an average particle size $D_{50}$ of about 1.0 to about 50 µm, preferably about 5.0 to about 45 µm, preferably about 10 to about 40 µm, about 14 to about 30 µm. The mean particle size $D_{50}$, for example, can be determined using dynamic light scattering (DLS).

Pigments with a specific shaping may also have been used to color the keratin material. For example, a pigment based on a lamellar and/or a lenticular substrate platelet can be used. Furthermore, coloring based on a substrate platelet including a vacuum metallized pigment is also possible.

In another particularly preferred embodiment, a process as contemplated herein is wherein the first composition (A) includes at least one colored pigment (A2) selected from the group of pigments based on a lamellar substrate platelet, pigments based on a lenticular substrate platelet, and pigments based on a substrate platelet including a vacuum metallized pigment.

The substrate platelets of this type have an average thickness of at most about 50 nm, preferably less than about 30 nm, particularly preferably at most about 25 nm, for example at most about 20 nm. The average thickness of the substrate platelets is at least about 1 nm, preferably at least about 2.5 nm, particularly preferably at least about 5 nm, for example at least about 10 nm. Preferred ranges for substrate wafer thickness are about 2.5 to about 50 nm, about 5 to about 50 nm, about 10 to about 50 nm; about 2.5 to about 30 nm, about 5 to about 30 nm, about 10 to about 30 nm; about 2.5 to about 25 nm, about 5 to about 25 nm, about 10 to about 25 nm, about 2.5 to about 20 nm, about 5 to about 20 nm, and about 10 to about 20 nm. Preferably, each substrate plate has a thickness that is as uniform as possible.

Due to the low thickness of the substrate platelets, the pigment exhibits particularly high hiding power.

The substrate plates have a monolithic structure. Monolithic in this context means including a single closed unit without fractures, stratifications or inclusions, although structural changes may occur within the substrate platelets. The substrate platelets are preferably homogeneously structured, i.e., there is no concentration gradient within the platelets. In particular, the substrate platelets do not have a layered structure and do not have any particles or particles distributed in them.

The size of the substrate platelet can be adjusted to the respective application purpose, especially the desired effect on the keratinic material. Typically, the substrate platelets have an average largest diameter of about about 2 to about 200 µm, especially about about 5 to about 100 µm.

In a preferred design, the aspect ratio, expressed by the ratio of the average size to the average thickness, is at least about 80, preferably at least about 200, more preferably at least about 500, more preferably more than about 750. The average size of the uncoated substrate platelets is the d50 value of the uncoated substrate platelets. Unless otherwise stated, the d50 value was determined using a Sympatec Helos device with quixel wet dispersion. To prepare the sample, the sample to be analyzed was pre-dispersed in isopropanol for 3 minutes.

The substrate platelets can be composed of any material that can be formed into platelet shape.

They can be of natural origin, but also synthetically produced. Materials from which the substrate platelets can be constructed include metals and metal alloys, metal oxides, preferably aluminum oxide, inorganic compounds and minerals such as mica and (semi-)precious stones, and plastics. Preferably, the substrate platelets are constructed of metal (alloy).

Any metal suitable for metallic luster pigments can be used. Such metals include iron and steel, as well as all air and water resistant (semi)metals such as platinum, zinc, chromium, molybdenum and silicon, and their alloys such as aluminum bronzes and brass. Preferred metals are aluminum, copper, silver and gold. Preferred substrate platelets include aluminum platelets and brass platelets, with aluminum substrate platelets being particularly preferred.

Lamellar substrate platelets are exemplified by an irregularly structured edge and are also referred to as "cornflakes" due to their appearance.

Due to their irregular structure, pigments based on lamellar substrate platelets generate a high proportion of scattered light. In addition, pigments based on lamellar substrate platelets do not completely cover the existing color of a keratinous material, and effects analogous to natural graying can be achieved, for example.

Lenticular (=lens-shaped) substrate platelets have a regular round edge and are also called "silver dollars" due to their appearance. Due to their regular structure, the proportion of reflected light predominates in pigments based on lenticular substrate platelets.

Vacuum metallized pigments (VMP) can be obtained, for example, by releasing metals, metal alloys or metal oxides from suitably coated films. They are exemplified by a particularly low thickness of the substrate platelets in the range of 5 to 50 nm and a particularly smooth surface with increased reflectivity. Substrate platelets including a vacuum metallized pigment are also referred to as VMP substrate platelets in the context of this application. VMP substrate platelets of aluminum can be obtained, for example, by releasing aluminum from metallized films.

The metal or metal alloy substrate plates can be passivated, for example by anodizing (oxide layer) or chromating.

Uncoated lamellar, lenticular and/or VPM substrate plates, especially those made of metal or metal alloy, reflect the incident light to a high degree and create a light-dark flop but no color impression.

A color impression can be created by optical interference effects, for example. Such pigments can be based on at least single-coated substrate platelets. These show interference effects by superimposing differently refracted and reflected light beams.

Accordingly, preferred pigments, pigments based on a coated lamellar substrate platelet. The substrate wafer preferably has at least one coating B of a highly refractive metal oxide having a coating thickness of at least about 50 nm. There is preferably another coating A between the coating B and the surface of the substrate wafer. If necessary, there is a further coating C on the layer B, which is different from the layer B underneath.

Suitable materials for coatings A, B and C are all substances that can be applied to the substrate platelets in a film-like and permanent manner and, in the case of coatings A and B, have the required optical properties. Coating part of the surface of the substrate platelets is sufficient to obtain a pigment with a glossy effect. For example, only the top and/or bottom of the substrate platelets may be coated, with the side surface(s) omitted. Preferably, the entire surface of the optionally passivated substrate platelets, including the side surfaces, is covered by coating B. The substrate platelets are thus completely enveloped by coating B. This improves the optical properties of the pigment and increases its mechanical and chemical resistance. The above also applies to layer A and preferably also to layer C, if present.

Although multiple coatings A, B and/or C may be present in each case, the coated substrate wafers preferably have only one coating A, B and, if present, C in each case.

The coating B is composed of at least one highly refractive metal oxide. Highly refractive materials have a refractive index of at least about 1.9, preferably at least about 2.0, and more preferably at least about 2.4. Preferably, the coating B includes at least about 95 wt. %, more preferably at least about 99 wt. %, of high refractive index metal oxide(s).

The coating B has a thickness of at least about 50 nm. Preferably, the thickness of coating B is no more than about 400 nm, more preferably no more than about 300 nm.

Highly refractive metal oxides suitable for coating B are preferably selectively light-absorbing (i.e., colored) metal oxides, such as iron(III) oxide (α- and γ-$Fe_2O_3$, red), cobalt (II) oxide (blue), chromium(III) oxide (green), titanium(III) oxide (blue, usually present in admixture with titanium oxynitrides and titanium nitrides), and vanadium(V) oxide (orange), and mixtures thereof. Colorless high-index oxides such as titanium dioxide and/or zirconium oxide are also suitable.

Coating B may contain a selectively absorbing dye, preferably 0.001 to 5% by weight, particularly preferably about 0.01 to about 1% by weight, in each case based on the total amount of coating B. Suitable dyes are organic and inorganic dyes which can be stably incorporated into a metal oxide coating.

The coating A preferably has at least one low refractive index metal oxide and/or metal oxide hydrate. Preferably, coating A includes at least 95 wt. %, more preferably at least 99 wt. %, of low refractive index metal oxide (hydrate). Low refractive index materials have a refractive index of 1.8 or less, preferably 1.6 or less.

Low refractive index metal oxides suitable for coating A include, for example, silicon (di)oxide, silicon oxide hydrate, aluminum oxide, aluminum oxide hydrate, boron oxide, germanium oxide, manganese oxide, magnesium oxide, and mixtures thereof, with silicon dioxide being preferred. The coating A preferably has a thickness of about 1 to about 100 nm, particularly preferably about 5 to about 50 nm, especially preferably about 5 to about 20 nm.

Preferably, the distance between the surface of the substrate platelets and the inner surface of coating B is at most about 100 nm, particularly preferably at most about 50 nm, especially preferably at most about 20 nm. By ensuring that the thickness of coating A, and thus the distance between the surface of the substrate platelets and coating B, is within the range specified above, it is possible to ensure that the pigments have a high hiding power.

If the pigment based on a lamellar substrate platelet has only one layer A, it is preferred that the pigment has a lamellar substrate platelet of aluminum and a layer A of silica. If the pigment based on a lamellar substrate platelet has a layer A and a layer B, it is preferred that the pigment has a lamellar substrate platelet of aluminum, a layer A of silica and a layer B of iron oxide.

According to a preferred embodiment, the pigments have a further coating C of a metal oxide (hydrate), which is different from the underlying coating B. Suitable metal oxides include silicon (di)oxide, silicon oxide hydrate, aluminum oxide, aluminum oxide hydrate, zinc oxide, tin oxide, titanium dioxide, zirconium oxide, iron (III) oxide, and chromium (III) oxide. Silicon dioxide is preferred.

The coating C preferably has a thickness of about 10 to about 500 nm, more preferably about 50 to about 300 nm. By providing coating C, for example based on $TiO_2$, better interference can be achieved while maintaining high hiding power.

Layers A and C serve as corrosion protection as well as chemical and physical stabilization. Particularly preferred layers A and C are silica or alumina applied by the sol-gel process. This process includes dispersing the uncoated lamellar substrate platelets or the lamellar substrate platelets already coated with layer A and/or layer B in a solution of a metal alkoxide such as tetraethyl orthosilicate or aluminum triisopropanolate (usually in a solution of organic solvent or a mixture of organic solvent and water with at least about 50% by weight of organic solvent such as a C1 to C4 alcohol) and adding a weak base or acid to hydrolyze the metal alkoxide, thereby forming a film of the metal oxide on the surface of the (coated) substrate platelets.

Layer B can be produced, for example, by hydrolytic decomposition of one or more organic metal compounds and/or by precipitation of one or more dissolved metal salts, as well as any subsequent post-treatment (for example, transfer of a formed hydroxide-including layer to the oxide layers by annealing).

Although each of the coatings A, B and/or C may be composed of a mixture of two or more metal oxide(hydrate)s, each of the coatings is preferably composed of one metal oxide(hydrate).

The pigments based on coated lamellar or lenticular substrate platelets, or the pigments based on coated VMP substrate platelets preferably have a thickness of about 70 to about 500 nm, particularly preferably about 100 to about 400 nm, especially preferably about 150 to about 320 nm, for example about 180 to about 290 nm. Due to the low thickness of the substrate platelets, the pigment exhibits particularly high hiding power. The low thickness of the coated substrate platelets is achieved by keeping the thickness of the uncoated substrate platelets low, but also by adjusting the thicknesses of the coatings A and, if present, C to as small a value as possible. The thickness of coating B determines the color impression of the pigment.

The adhesion and abrasion resistance of pigments based on coated substrate platelets in keratinic material can be significantly increased by additionally modifying the outermost layer, layer A, B or C depending on the structure, with organic compounds such as silanes, phosphoric acid esters, titanates, borates or carboxylic acids. In this case, the organic compounds are bonded to the surface of the outermost, preferably metal oxide-including, layer A, B, or C. The outermost layer denotes the layer that is spatially farthest from the lamellar substrate platelet. The organic compounds are preferably functional silane compounds that can bind to the metal oxide-including layer A, B, or C. These can be either mono- or bifunctional compounds. Examples of bifunctional organic compounds include methacryloxy-propenyltrimethoxysilane, 3-methacryloxypropyltrimethoxysilane, 3-acryloxypropyltrimethoxysilane, 2-acryloxyethyltrimethoxysilane, 3-methacryloxy-propyltriethoxysilane, 3-acryloxypropyltrimethoxysilane, 2-methacryloxyethyl-triethoxysilane, 2-acryloxyethyltriethoxysilane, 3-methacryloxypropyltris(methox-yethoxy)silane, 3-methacryloxypropyltris(butoxyethoxy)silane, 3-methacryloxy-propyltris(propoxy)silane, 3-methacryloxypropyltris(butoxy)silane, 3-acryloxy-propyltris(methoxyethoxy)silane, 3-acryloxy-propyltris(butoxyethoxy)silane, 3-acryl-oxypropyltris(butoxy)silane, vinyltrimethoxysilane, vinyltriethoxysilane, vinylethyl dichlorosilane, vinylmethyldiacetoxysilane, vinylmethyldichlorosilane, vinylmethyldiethoxysilane, vinyltriacetoxysilane, vinyltrichlorosilane, phenylvinyldiethoxysilane, or phenylallyldichlorosilane. Furthermore, a modification with a monofunctional silane, an alkylsilane or arylsilane, can be conducted. This has only one functional group, which can covalently bond to the surface pigment based on coated lamellar substrate platelets (i.e., to the outermost metal oxide-including layer) or, if not completely covered, to the metal surface. The hydrocarbon residue of the silane points away from the pigment. Depending on the type and nature of the hydrocarbon residue of the silane, a varying degree of hydrophobicity of the pigment is achieved. Examples of such silanes include hexadecyltrimethoxysilane, propyltrimethoxysilane, etc. Particularly preferred are pigments based on silica-coated aluminum substrate platelets surface-modified with a monofunctional silane. Octyltrimethoxysilane, octyltriethoxysilane, hecadecyltrimethoxysilane and hecadecyltriethoxysilane are particularly preferred. Due to the changed surface properties/hydrophobization, an improvement can be achieved in terms of adhesion, abrasion resistance and alignment in the application.

Suitable pigments based on a lamellar substrate platelet include, for example, the pigments of the VISIONAIRE series from Eckart.

Pigments based on a lenticular substrate platelet are available, for example, under the name Alegrace® Gorgeous from the company Schlenk Metallic Pigments GmbH.

Pigments based on a substrate platelet including a vacuum metallized pigment are available, for example, under the name Alegrace® Marvelous or Alegrace® Aurous from the company Schlenk Metallic Pigments GmbH.

In a further embodiment, a process as contemplated herein is wherein the composition (A) includes—based on the total weight of the composition (A)—one or more pigments in a total amount of from about 0.001 to about 20% by weight, from about 0.05 to about 5% by weight.

As colorant compounds, the compositions as contemplated herein may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments. Preferably, the direct dyes within the meaning of the present disclosure have a solubility in water (760 mmHg) at 25° C. of more than 1.0 g/L. In particular, the direct dyes within the meaning of the present disclosure have a solubility in water (760 mmHg) at 25° C. of more than 1.5 g/L.

Direct dyes can be divided into anionic, cationic and nonionic direct dyes.

In a further preferred embodiment, an agent as contemplated herein is wherein it includes at least one anionic, cationic and/or nonionic direct dye as the coloring compound.

In a further preferred embodiment, a process as contemplated herein is wherein the composition (B) and/or the composition (C) includes at least one colorant compound selected from the group of anionic, nonionic, and/or cationic direct dyes.

Suitable cationic direct dyes include Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4- [(2-hydroxyethyl)amino]—3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2- [(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—COO—, —SO$_3$ present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (760 mmHg) at 25° C. of more than about 0.5 g/L and are therefore not to be regarded as pigments. Preferably the acid dyes within the meaning of the present disclosure have a solubility in water (760 mmHg) at 25° C. of more than about 1.0 g/L.
The alkaline earth salts (such as calcium salts and magnesium salts) or aluminum salts of acid dyes often have a lower solubility than the corresponding alkali salts. If the solubility of these salts is below about 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

For example, one or more compounds from the following group can be selected as particularly well suited acid dyes: Acid Yellow 1 (D&C Yellow 7, Citronin A, Ext. D&C Yellow No. 7, Japan Yellow 403,CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1;CI 20170;KATSU201; nosodiumsalt;Brown No. 201;RESORCIN BROWN;ACID ORANGE 24;Japan Brown 201;D & C Brown No. 1), Acid Red 14 (C.I.14720), Acid Red 18 (E124, Red 18; CI 16255), Acid Red 27 (E 123, CI 16185, C-Rot 46, Real red D, FD&C Red Nr.2, Food Red 9, Naphthol red S), Acid Red 33 (Red 33, Fuchsia Red, D&C Red 33, CI 17200), Acid Red 35 (CI C.I.18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red n°° 106 Pontacyl Brilliant Pink), Acid Red 73 (CI 27290), Acid Red 87 (Eosin, CI 45380), Acid Red 92 (COLIPA n° C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet n°° 2, C.I. 60730, COLIPA n° C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreenl), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n°° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C. Acid Orange 7 is the sodium salt of 4-[(2-hydroxy-1-naphthyl)azo]benzene sulphonate. Its water solubility is more than 7 g/L (25° C.).

Acid Red 18 is the trinatirum salt of 7-hydroxy-8-[(E)-(4-sulfonato-1-naphthyl)-diazenyl)]-1,3-naphthalene disulfonate and has an extremely high water solubility of more than 20% by weight.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino}phenyl}{4-[(N-ethyl(3-sulfonatobenzyl)imino]-2,5-cyclohexadien-1-ylidene}methyl)-benzenesulfonate and has a solubility in water of more than 20% by weight (25° C.).

Thermochromic dyes can also be used. Thermochromism involves the property of a material to change its color reversibly or irreversibly as a function of temperature. This can be done by changing both the intensity and/or the wavelength maximum.

Finally, it is also possible to use photochromic dyes. Photochromism involves the property of a material to reversibly or irreversibly change its color depending on irradiation with light, especially UV light. This can be done by changing both the intensity and/or the wavelength maximum.

In a further embodiment, a process as contemplated herein is wherein the composition (A) includes—based on the total weight of the composition (A)—one or more direct dyes in a total amount of from 0.001 to 20% by weight, from 0.05 to 5% by weight. Other cosmetic ingredients in the composition (A)

In addition, the composition (A) may also contain one or more other cosmetic ingredients.

The cosmetic ingredients that may be optionally used in the composition (A) may be any suitable ingredients to impart further beneficial properties to the product. For example, in the composition (A), a solvent, a thickening or film-forming polymer, a surface-active compound from the group of nonionic, cationic, anionic or zwitterionic/amphoteric surfactants, the coloring compounds from the group of pigments, the direct dyes, oxidation dye precursors, fatty components from the group of $C_8$-$C_{30}$ fatty alcohols, hydrocarbon compounds, fatty acid esters, acids and bases belonging to the group of pH regulators, perfumes, preservatives, plant extracts and protein hydrolysates.

The selection of these other substances will be made by the specialist according to the desired properties of the agents. Regarding other optional components and the quantities of these components used, explicit reference is made to the relevant manuals known to the specialist.

In this context, it has proved particularly preferred to use in composition (A) a cosmetic ingredient selected from the group of hexamethyldisiloxane, octamethyltrisiloxane, decamethyltetrasiloxane, hexamethylcyclotrisiloxane, octamethylcyclotetrasiloxane and/or decamethylcyclopentasiloxane.

In another particularly preferred embodiment, a process as contemplated herein is wherein the first composition (A) includes at least one cosmetic ingredient selected from the group of hexamethyldisiloxane. includes octamethyltrisiloxane, decamethyltetrasiloxane, hexamethylcyclotrisiloxane, octamethylcyclotetrasiloxane and decamethylcyclopentasiloxane. Hexamethyldisiloxane has the CAS number 107-46-0 and can be purchased commercially from Sigma-Aldrich, for example.

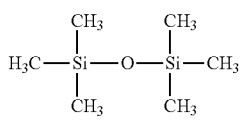

Octamethyltrisiloxane has the CAS number 107-51-7 and is also commercially available from Sigma-Aldrich.

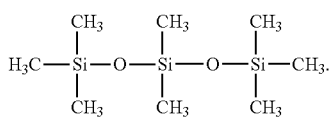

Decamethyltetrasiloxane carries the CAS number 141-62-8 and is also commercially available from Sigma-Aldrich.

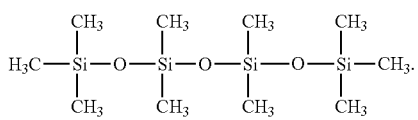

Hexamethylcyclotrisiloxane has the CAS No. 541-05-9.
Octamethylcyclotetrasiloxane has the CAS No. 556-67-2.
Decamethylcyclopentasiloxane has the CAS No. 541-02-6.

The use of hexamethyldisiloxane in composition (A) has proved to be particularly preferred. Particularly preferably, hexamethyldisiloxane is present—based on the total weight of composition (A)—in amounts of from about 1.0 to about 20.0% by weight, preferably from about 1.3 to about 10.0% by weight, further preferably from about 1.6 to about 5.0% by weight and very particularly preferably from about 2.0 to about 4.0% by weight in composition (A).

Water Content (A1) in the Composition (A)

The process as contemplated herein is exemplified by the application of a first composition (A) on the keratinous material.

In the context of the present disclosure, composition (A) means a ready-to-use composition which, in its present embodiment, can be applied to the keratin material to the hair.

In the process as contemplated herein, the composition (A) can be provided in its present form in a container. However, with the $C_1$-$C_6$ alkoxy silanes, the composition (A) includes very reactive compounds. However, to avoid problems related to storage stability, it is particularly preferred to prepare the ready-to-use and reactive composition (A) just before use by mixing two or more storage-stable compositions. For example, the ready-to-use composition (A) can be prepared by mixing a low-water silane blend (A-I), which includes the organic $C_1$-$C_6$ alkoxy silane(s) (A1) in concentrated form, and a water-rich carrier formulation (A-II), which can be, for example, a gel, a lotion or a surfactant system.

Accordingly, the ready-to-use composition (A) preferably has a higher water content, which—based on the total weight of the composition (A)—may be in the range from about 50.0 to about 90.0% by weight, preferably from about 55.0 to about 90.0% by weight, further preferably from about 60.0 to about 90.0% by weight and particularly preferably from about 70.0 to about 90.0% by weight.

In the context of a further embodiment, a process as contemplated herein is wherein the first composition (A) includes—based on the total weight of the composition (A)—from about 50.0 to about 90.0% by weight, preferably from about 55.0 to about 90.0% by weight, further preferably from 60.0 to 90.0% by weight and particularly preferably from about 70.0 to about 90.0% by weight of water.

pH Value of the Compositions (A)

In further experiments it has been found that the pH values of composition (A) can have an influence on the color intensities obtained during dyeing. It was found that alkaline pH values have a beneficial effect on the dyeing performance achievable in the process.

For this reason, it is preferred that the compositions (A) have a pH of from about 7.0 to about 12.0, preferably from about 7.5 to about 11.5, more preferably from about 8.0 to about 11.0, and most preferably from about 8.0 to about 10.5.

The pH value can be measured using the usual methods known from the state of the art, such as pH measurement using glass electrodes via combination electrodes or using pH indicator paper.

In another very particularly preferred embodiment, a process as contemplated herein, wherein the composition (A) has a pH of from about 7.0 to about 12.0, preferably from about 7.5 to about 11.5, more preferably from about 8.0 to about 11.0 and most preferably from about 8.0 to about 10.5.

To adjust the above pH values, the alkalizing agents can be used, which can also be used to adjust the pH value of composition (B).

Alkalizing Agent (B1) in the Composition (B)

As an ingredient (B1) essential to the present disclosure, the composition (B) includes at least one alkalizing agent.

Particularly preferably, the alkalizing agent is selected from the group of ammonia, $C_2$-$C_6$ alkanolamines, basic amino acids, alkali metal hydroxides and alkaline earth metal hydroxides.

In the context of a further particularly preferred embodiment, a process as contemplated herein is wherein the composition (B) includes at least one alkalizing agent (B1) selected from the group of ammonia, $C_2$-$C_6$ alkanolamines, basic amino acids, alkali metal hydroxides, alkaline earth metal hydroxides, alkali metal silicates, alkali metal metasilicates, alkaline earth metal silicates, alkaline earth metal metasilicates, alkali metal carbonates and alkaline earth metal carbonates.

It has been found that post-treatment with a composition (B) including ammonia exerts a particularly good influence on improving the wash fastness and rub fastness of the dyeing obtained in the process.

In the context of a further very particularly preferred embodiment, a process as contemplated herein is wherein the composition (B) includes ammonia as alkalizing agent (B1).

Satisfactory results were also obtained when the composition (B) included at least one $C_2$-$C_6$ alkanolamine as alkalizing agent (B1).

The alkanolamines that can be used in composition (B) can be selected, for example, from the group of primary amines having a $C_2$-$C_6$ alkyl parent carrying at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

In a further preferred embodiment, a process as contemplated herein is wherein the composition (B) includes at least one alkalizing agent (B1) from the group of alkanolamines, which is preferably selected from the group of 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol and 2-amino-2-methylpropane-1,3-diol.

Likewise, satisfactory results were obtained when composition (B) included at least one basic amino acid as alkalizing agent (a2).

For the purposes of the present disclosure, an amino acid is an organic compound including in its structure at least one protonatable amino group and at least one —COOH or one —$SO_3H$ group. Preferred amino acids are aminocarboxylic acids, especially α-(alpha)— aminocarboxylic acids and ω-aminocarboxylic acids, whereby α-aminocarboxylic acids are particularly preferred.

As contemplated herein, basic amino acids are those amino acids which have an isoelectric point pI of greater than 7.0.

Basic α-aminocarboxylic acids contain at least one asymmetric carbon atom. In the context of the present disclosure, both enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred embodiment, an agent as contemplated herein is therefore wherein the alkalizing agent is a basic amino acid from the group arginine, lysine, ornithine and/or histidine.

In a further preferred embodiment, a process as contemplated herein is wherein the composition (B) includes at least one alkalizing agent (B1) from the group of basic amino acids, which is preferably selected from the group of arginine, lysine, ornithine and histidine.

Satisfactory results were also obtained when the composition (B) included at least one alkali metal hydroxide as alkalizing agent (B1). Suitable alkali metal hydroxides include sodium hydroxide and potassium hydroxide.

Satisfactory results were also obtained when the composition (B) included at least one alkaline earth metal hydroxide as alkalizing agent (B1). Suitable alkaline earth metal hydroxides include magnesium hydroxide, calcium hydroxide and barium hydroxide.

Likewise, satisfactory results were obtained when the composition (B) included at least one alkali metal silicate and/or alkali metal metasilicate as alkalizing agent (B1). Suitable alkali metal silicates include sodium silicate and potassium silicate. Suitable alkali metal metasilicates include sodium metasilicate and potassium metasilicate.

Satisfactory results were also obtained when the composition (B) included at least one alkali metal carbonate and/or alkaline earth metal carbonate as alkalizing agent (B1). Suitable alkali metal carbonates include sodium carbonate and potassium carbonate. Suitable alkaline earth metal carbonates include magnesium carbonate and calcium carbonate.

Ammonia, $C_2$-$C_6$ alkanolamines, basic amino acids and alkali metal hydroxides have proved to be particularly suitable within the group of alkali metal agents (B1) mentioned above.

In the context of a further particularly preferred embodiment, a process as contemplated herein is wherein the composition (B) includes at least one alkalizing agent (B1) selected from the group of ammonia, $C_2$-$C_6$ alkanolamines, basic amino acids and alkali metal hydroxides.

In the context of a further particularly preferred embodiment, a process as contemplated herein is wherein the composition (B) includes at least one alkalizing agent (B1) selected from the group of ammonia, 2-aminoethan-1-ol, 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide and potassium hydroxide.

Water Content of the Composition (B)

The composition (B) includes the alkali agent(s) (B1) in a cosmetic carrier, preferably in an aqueous cosmetic carrier.

In this context, it has been found to be preferred if the composition (B) includes -based on the total weight of the composition (B)—about 5.0 to about 99.0% by weight, preferably about 15.0 to about 97.0% by weight, more preferably about 25.0 to about 97.0% by weight, still more preferably about 35.0 to about 97.0% by weight and very particularly preferably about 45.0 to about 97.0% by weight of water.

In a further embodiment, a process as contemplated herein is wherein the second composition (B) includes—based on the total weight of the composition (B)—from about 5.0 to about 99.0% by weight, preferably from about 15.0 to about 97.0% by weight, more preferably from about 25.0 to about 97.0% by weight, still more preferably from about 35.0 to about 97.0% by weight and very particularly preferably from about 45.0 to about 97.0% by weight of water.

pH Value of the Compositions (B)

The alkalizing agents included in the composition (B) exert an influence on the pH value of the composition. It was found that alkaline pH values have a beneficial effect on the dyeing performance achievable in the process and the fastness properties of the dyeings.

For this reason, it is preferred that the compositions (B) have a pH of from about 7.0 to about 12.0, preferably from about 7.5 to about 11.5, more preferably from about 8.0 to about 11.0, and most preferably from about 8.0 to about 10.5.

The pH value can be measured using the usual methods known from the state of the art, such as pH measurement using glass electrodes via combination electrodes or using pH indicator paper.

In another very particularly preferred embodiment, a process as contemplated herein, wherein the composition (B) has a pH of from about 7.0 to about 12.0, preferably from about 7.5 to about 11.5, more preferably from about 8.0 to about 11.0, and most preferably from about 8.0 to 10.5.

To adjust this alkaline pH, it may be necessary to add an alkalizing agent and/or acidifying agent to the reaction mixture. The pH values for the purposes of the present disclosure are pH values measured at a temperature of 22° C.

Film-Forming Polymers in the Composition (B)

The composition (B) may further additionally include at least one film-forming polymer Polymers are macromolecules with a molecular weight of at least about 1000 g/mol, preferably of at least about 2500 g/mol, particularly preferably of at least about 5000 g/mol, which include identical, repeating organic units. The polymers of the present disclosure may be synthetically produced polymers which are manufactured by polymerization of one type of monomer or by polymerization of several types of monomer which are structurally different from each other. If the polymer is produced by polymerizing a type of monomer, it is called a homo-polymer. If structurally different monomer types are used in polymerization, the resulting polymer is called a copolymer.

The maximum molecular weight of the polymer depends on the degree of polymerization (number of polymerized monomers) and the batch size and is determined by the polymerization method. For the purposes of the present disclosure, it is preferred that the maximum molecular weight of the film-forming hydrophobic polymer (c) is not more than 107 g/mol, preferably not more than 106 g/mol and particularly preferably not more than 105 g/mol.

In the context of the present disclosure, a film-forming polymer is a polymer which can form a film on a substrate, for example on a keratinic material or a keratinic fiber. The formation of a film can be demonstrated, for example, by looking at the keratin material treated with the polymer under a microscope.

In a further preferred embodiment, a process as contemplated herein is wherein the second composition (B) includes at least one film-forming polymer.

In a further particularly preferred embodiment, a process as contemplated herein is wherein the second composition (B) includes at least one film-forming polymer preferably selected from the group of homopolymers or copolymers of acrylic acid, methacrylic acid, acrylic esters, methacrylic esters, acrylic amides, methacrylic amides, vinylpyrrolidone, vinyl alcohol, vinyl acetate, ethylene, propylene, styrene, polyurethanes, polyesters and/or polyamides.

The film-forming polymers can be hydrophilic or hydrophobic.

In a first embodiment, it may be preferred to use in the composition (B), at least one hydrophobic film-forming polymer.

A hydrophobic polymer is a polymer that has a solubility in water at 25° C. (760 mmHg) of less than about 1% by weight.

The water solubility of the film-forming, hydrophobic polymer can be determined in the following way, for example. 1.0 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. If the polymer-water mixture cannot be assessed visually due to a high turbidity of the mixture, the mixture is filtered. If a proportion of undissolved polymer remains on the filter paper, the solubility of the polymer is less than 1% by weight.

These include acrylic acid-type polymers, polyurethanes, polyesters, polyamides, polyureas, cellulose polymers, nitrocellulose polymers, silicone polymers, acrylamide-type polymers and polyisoprenes.

Particularly well suited film-forming, hydrophobic polymers are, for example, polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In a further preferred embodiment, an agent as contemplated herein is wherein it includes at least one film-forming hydrophobic polymer (c) selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

The film-forming hydrophobic polymers, which are selected from the group of synthetic polymers, polymers obtainable by radical polymerization or natural polymers, have proved to be particularly suitable for solving the problem as contemplated herein.

Other particularly well-suited film-forming hydrophobic polymers can be selected from the homopolymers or copolymers of olefins, such as cycloolefins, butadiene, isoprene or styrene, vinyl ethers, vinyl amides, the esters or amides of (meth)acrylic acid having at least one $C_1$-$C_{20}$ alkyl group, an aryl group or a $C_2$-$C_{10}$ hydroxyalkyl group.

Other film-forming hydrophobic polymers may be selected from the homo- or copolymers of isooctyl (meth) acrylate; isonononyl (meth)acrylate; 2-ethylhexyl (meth) acrylate; lauryl (meth)acrylate; isopentyl (meth)acrylate; n-butyl (meth)acrylate); isobutyl (meth)acrylate; ethyl (meth)acrylate; methyl (meth)acrylate; tert-butyl (meth) acrylate; stearyl (meth)acrylate; hydroxyethyl (meth)acrylate; 2-hydroxypropyl (meth)acrylate; 3-hydroxypropyl (meth)acrylate and/or mixtures thereof.

Other film-forming hydrophobic polymers may be selected from the homo- or copolymers of (meth)acrylamide; N-alkyl-(meth)acrylamides, in those with C2-C18 alkyl groups, such as N-ethyl-acrylamide, N-tert-butyl-acrylamide, le N-octyl-crylamide; N-di(C1-C4)alkyl-(meth)acrylamide.

Other preferred anionic copolymers are, for example, copolymers of acrylic acid, methacrylic acid or their $C_1$-$C_6$ alkyl esters, as they are marketed under the INCI Declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Very particularly preferred polymers on the market are, for example, Aculyn® 22 (Acrylates/Steareth-20 Me-thacrylate Copolymer), Aculyn® 28 (Acrylates/Beheneth-25 Methacrylate Copolymer), Structure 2001@ (Acryla-tes/Steareth-20 Itaconate Copolymer), Structure 3001@ (Acrylates/Ceteth-20 Itaconate Copolymer), Structure Plus® (Acrylates/Aminoacrylates C10-30 Alkyl PEG-20 Itaconate Copolymer), Carbopol® 1342, 1382, Ultrez 20, Ultrez 21 (Acrylates/C10-30 Alkyl Acrylate Crosspolymer), Synthalen W 2000® (Acrylates/Palmeth-25 Acrylate Copolymer) or the Rohme und Haas distributed Soltex OPT (Acrylates/C12-22 Alkyl methacrylate Copolymer).

The homo- and copolymers of N-vinylpyrrolidone, vinylcaprolactam, vinyl-(C1-C6)alkyl-pyrrole, vinyl-oxazole, vinyl-thiazole, vinylpyrimidine, vinylimidazole can be named as suitable polymers based on vinyl monomers.

Furthermore, the copolymers octylacrylamide/acrylates/butylaminoethyl-methacrylate copolymer, as commercially marketed under the trade names AMPHOMER® or LOVOCRYL® 47 by NATIONAL STARCH, or the copolymers of acrylates/octylacrylamides marketed under the trade names DERMACRYL® LT and DERMACRYL® 79 by NATIONAL STARCH are particularly suitable.

Suitable olefin-based polymers include homopolymers and copolymers of ethylene, propylene, butene, isoprene and butadiene.

In another embodiment, the film-forming hydrophobic polymers may be the block copolymers including at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

Intensive and washfast staining could also be obtained when the composition (B) included at least one film-forming polymer selected from the group of acrylic acid homopolymers and copolymers, methacrylic acid homopolymers and copolymers, acrylic acid ester homopolymers and copolymers, methacrylic acid ester homopolymers and copolymers, acrylic acid amide homopolymers and copolymers, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further preferred embodiment, a process as contemplated herein is wherein the composition (B) includes at least one film-forming polymer selected from the group of the homopolymers and copolymers of acrylic acid, the homopolymers and copolymers of methacrylic acid, the homopolymers and copolymers of acrylic acid esters, the homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a first embodiment, it may be preferred to use at least one hydrophilic film-forming polymer in the composition (B).

A hydrophilic polymer is a polymer that has a solubility in water at 25° C. (760 mmHg) of more than about 1% by weight, preferably more than about 2% by weight.

The water solubility of the film-forming, hydrophilic polymer can be determined in the following way, for example. 1.0 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. A completely dissolved polymer appears marcoscopically homogeneous. If the polymer-water mixture cannot be assessed visually due to a high turbidity of the mixture, the mixture is filtered. If no undissolved polymer remains on the filter paper, the solubility of the polymer is more than markoscopically 1% by weight.

Nonionic, anionic and cationic polymers can be used as film-forming, hydrophilic polymers.

Suitable film-forming hydrophilic polymers can be selected, for example, from the group of polyvinylpyrrolidone (co)polymers, polyvinyl alcohol (co)polymers, vinyl acetate (co)polymers, carboxyvinyl (co)polymers, acrylic acid (co)polymers, methacrylic acid (co)polymers, natural gums, polysaccharides and/or acrylamide (co)polymers.

Furthermore, it is particularly preferred to use polyvinylpyrrolidone (PVP) and/or a vinylpyrrolidone-including copolymer as film-forming hydrophilic polymer.

In another particularly preferred embodiment, an agent as contemplated herein is wherein it includes (c) at least one film-forming, hydrophilic polymer selected from the group of polyvinylpyrrolidone (PVP) and the copolymers of polyvinylpyrrolidone.

It is further preferred if the agent as contemplated herein includes polyvinylpyrrolidone (PVP) as the film-forming hydrophilic polymer. Surprisingly, the wash fastness of the dyeing obtained with agents including PVP (b9 was also particularly good.

Particularly well-suited polyvinylpyrrolidones are available, for example, under the name Luviskol® K from BASF SE, especially Luviskol® K 90 or Luviskol® K 85 from BASF SE.

The polymer PVP K30, which is marketed by Ashland (ISP, POI Chemical), can also be used as another explicitly very well suited polyvinylpyrrolidone (PVP). PVP K 30 is a polyvinylpyrrolidone which is highly soluble in cold water and has the CAS number 9003-39-8. The molecular weight of PVP K 30 is about 40000 g/mol.

Other particularly suitable polyvinylpyrrolidones are the substances known under the trade names LUVITEC K 17, LUVITEC K 30, LUVITEC K 60, LUVITEC K 80, LUVITEC K 85, LUVITEC K 90 and LUVITEC K 115 and available from BASF.

The use of film-forming hydrophilic polymers from the group of copolymers of polyvinylpyrrolidone has also led to particularly good and washfast color results.

Vinylpyrrolidone-vinyl ester copolymers, such as those marketed under the trademark Luviskol® (BASF), are particularly suitable film-forming hydrophilic polymers. Luviskol® VA 64 and Luviskol® VA 73, both vinylpyrrolidone/vinyl acetate copolymers, are particularly preferred non-ionic polymers.

Of the vinylpyrrolidone-including copolymers, a styrene/VP copolymer and/or a vinylpyrrolidone-vinyl acetate copolymer and/or a VP/DMAPA acrylates copolymer and/or a VP/vinyl caprolactam/DMAPA acrylates copolymer are particularly preferred in cosmetic compositions.

Vinylpyrrolidone-vinyl acetate copolymers are marketed under the name Luviskol® VA by BASF SE. For example, a VP/Vinyl Caprolactam/DMAPA Acrylates copolymer is sold under the trade name Aquaflex® SF-40 by Ashland Inc. For example, a VP/DMAPA acrylates copolymer is marketed by Ashland under the name Styleze CC-10 and is a highly preferred vinylpyrrolidone-including copolymer.

Other suitable copolymers of polyvinylpyrrolidone may also be those obtained by reacting N-vinylpyrrolidone with at least one further monomer from the group including of V-vinylformamide, vinyl acetate, ethylene, propylene, acrylamide, vinylcaprolactam, vinylcaprolactone and/or vinyl alcohol.

In another very particularly preferred embodiment, an agent as contemplated herein is wherein it includes at least one film-forming, hydrophilic polymer selected from the group of polyvinylpyrrolidone (PVP), vinylpyrrolidone/vinyl acetate copolymers, vinylpyrrolidone/styrene copolymers, vinylpyrrolidone/ethylene copoylmeres, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers.

Another suitable copolymer of vinylpyrrolidone is the polymer known under the INCI designation maltodextrin/VP copolymer.

Furthermore, intensively dyed keratin material, especially hair, with particularly good wash fastness could be obtained if a non-ionic, film-forming, hydrophilic polymer was used as the film-forming, hydrophilic polymer.

In a first embodiment, it may be preferred if the composition (B) includes at least one nonionic, film-forming, hydrophilic polymer.

As contemplated herein, a non-ionic polymer is understood to be a polymer which in a protic solvent—such as water—under standard conditions does not carry structural units with permanent cationic or anionic groups, which must be compensated by counterions while maintaining electron neutrality. Cationic groups include quaternized ammonium groups but not protonated amines. Anionic groups include carboxylic and sulphonic acid groups.

Preference is given to products including, as a non-ionic, film-forming, hydrophilic polymer, at least one polymer selected from the group of
Polyvinylpyrrolidone,
Copolymers of N-vinylpyrrolidone and vinyl esters of carboxylic acids having 2 to 18 carbon atoms of N-vinylpyrrolidone and vinyl acetate,
Copolymers of N-vinylpyrrolidone and N-vinylimidazole and methacrylamide,
Copolymers of N-vinylpyrrolidone and N-vinylimidazole and acrylamide,
Copolymers of N-vinylpyrrolidone with N,N-di(C1 to C4)-alkylamino-(C2 to C4)-alkylacrylamide, If copolymers of N-vinylpyrrolidone and vinyl acetate are used, it is again preferable if the molar ratio of the structural units included in the monomer N-vinylpyrrolidone to the structural units of the polymer included in the monomer vinyl acetate is in the range from 20:80 to 80:20, in particular from 30:70 to 60:40. Suitable copolymers of vinyl pyrrolidone and vinyl acetate are available, for example, under the trademarks Luviskol® VA 37, Luviskol® VA 55, Luviskol® VA 64 and Luviskol® VA 73 from BASF SE.

Another particularly preferred polymer is selected from the INCI designation VP/Methacrylamide/Vinyl Imidazole Copolymer, which is available under the trade name Luviset Clear from BASF SE.

Another particularly preferred non-ionic, film-forming, hydrophilic polymer is a copolymer of N-vinylpyrrolidone and N,N-dimethylaminiopropylmethacrylamide, which is sold under the INCI designation VP/DMAPA Acrylates Copolymer e.g., under the trade name Styleze® CC 10 by ISP.

A cationic polymer of interest is the copolymer of N-vinylpyrrolidone, N-vinylcaprolactam, N-(3-dimethylaminopropyl)methacrylamide and 3-(methacryloylamino)propyl-lauryl-dimethylammonium chloride (INCI designation): Polyquatemium-69), which is marketed, for example, under the trade name AquaStyle® 300 (28-32 wt. % active substance in ethanol-water mixture, molecular weight 350000) by ISP.

Other Suitable Film-Forming, Hydrophilic Polymers Include
Vinylpyrrolidone-vinylimidazolium methochloride copolymers, as offered under the designations Luviquat© FC 370, FC 550 and the INCI designation Polyquaternium-16 as well as FC 905 and HM 552,
Vinylpyrrolidone-vinylcaprolactam-acrylate terpolymers, as they are commercially available with acrylic acid esters and acrylic acid amides as a third monomer component, for example under the name Aquaflex® SF 40.

Polyquaternium-11 is the reaction product of diethyl sulphate with a copolymer of vinyl pyrrolidone and dimethylaminoethyl methacrylate. Suitable commercial products are available under the names Dehyquart® CC 11 and Luviquat® PQ 11 PN from BASF SE or Gafquat 440, Gafquat 734, Gafquat 755 or Gafquat 755N from Ashland Inc.

Polyquaternium-46 is the reaction product of vinylcaprolactam and vinylpyrrolidone with methylvinylimidazolium methosulfate and is available for example under the name Luviquat® Hold from BASF SE. Polyquaternium-46 is preferably used in an amount of 1 to 5% by weight—based on the total weight of the cosmetic composition. It particularly prefers to use polyquaternium-46 in combination with a cationic guar compound. It is even highly preferred that polyquaternium-46 is used in combination with a cationic guar compound and polyquaternium-11.

Suitable anionic film-forming, hydrophilic polymers can be, for example, acrylic acid polymers, which can be in non-crosslinked or crosslinked form. Such products are sold commercially under the trade names Carbopol 980, 981, 954, 2984 and 5984 by Lubrizol or under the names Synthalen M and Synthalen K by 3V Sigma (The Sun Chemicals, Inter Harz).

Examples of suitable film-forming, hydrophilic polymers from the group of natural gums are xanthan gum, gellan gum, carob gum.

Examples of suitable film-forming hydrophilic polymers from the group of polysaccharides are hydroxyethyl cellulose, hydroxypropyl cellulose, ethyl cellulose and carboxymethyl cellulose.

Suitable film-forming, hydrophilic polymers from the group of acrylamdes are, for example, polymers which are produced from monomers of (methy)acrylamido-C1-C4-alkyl sulphonic acid or the salts thereof. Corresponding polymers may be selected from the polymers of polyacrylamidomethanesulfonic acid, polyacrylamidoethanesulfonic acid, polyacrylamidopropanesulfonic acid, poly2-acrylamido-2-methylpropanesulfonic acid, poly-2-methylacrylamido-2-methylpropanesulfonic acid and/or poly-2-methylacrylamido-n-butanesulfonic acid.

Preferred polymers of the poly(meth)arylamido-C1-C4-alkyl sulphonic acids are cross-linked and at least about 90% neutralized. These polymers can or cannot be cross-linked.

Cross-linked and fully or partially neutralized polymers of the poly-2-acrylamido-2-methylpropane sulfonic acid type are available under the INCI designation "Ammonium Polyacrylamido-2-methyl-propanesulphonates" or "Ammonium Poly acryldimethyltauramides".

Another preferred polymer of this type is the cross-linked poly-2-acrylamido-2-methyl-propanesulphonic acid polymer marketed by Clamant under the trade name Hostacerin AMPS, which is partially neutralized with ammonia.

In another explicitly quite particularly preferred embodiment, a process as contemplated herein is wherein the composition (B) includes at least one anionic, film-forming, polymer.

In this context, the best results were obtained when the composition (B), includes at least one film-forming polymer including at least one structural unit of formula (P-I) and at least one structural unit of formula (P-II)

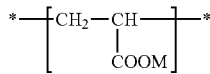

(P-I)

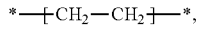

(P-II)

where
M is a hydrogen atom or ammonium (NH$_4$), sodium, potassium, ½ magnesium or ½ calcium.
When M represents a hydrogen atom, the structural unit of the formula (P-I) is based on an acrylic acid unit.
When M stands for an ammonium counterion, the structural unit of the formula (P-I) is based on the ammonium salt of acrylic acid.
When M stands for a sodium counterion, the structural unit of the formula (P-I) is based on the sodium salt of acrylic acid.
When M stands for a potassium counterion, the structural unit of the formula (P-I) is based on the potassium salt of acrylic acid.
If M stands for a half equivalent of a magnesium counterion, the structural unit of the formula (P-I) is based on the magnesium salt of acrylic acid.
If M stands for a half equivalent of a calcium counterion, the structural unit of the formula (P-I) is based on the calcium salt of acrylic acid.

The film-forming polymer or polymers as contemplated herein are preferably used in certain ranges of amounts in the composition (B) as contemplated herein. In this context, it has proved particularly preferable for solving the problem as contemplated herein if the composition (B) includes—in each case based on its total weight—one or more film-forming polymers in a total amount of from about 0.1 to about 18.0% by weight, preferably from about 1.0 to about 16.0% by weight, more preferably from about 5.0 to about 14.5% by weight and very particularly preferably from about 8.0 to about 12.0% by weight.

In a further preferred embodiment, a process as contemplated herein is wherein the composition (B) includes—based on its respective total weight—one or more film-forming polymers in a total amount of from about 0.1 to about 18.0% by weight, preferably from about 1.0 to about 16.0% by weight, more preferably from about 5.0 to about 14.5% by weight and very particularly preferably from about 8.0 to about 12.0% by weight.

Other Cosmetic Ingredients in the Composition (B)

In addition, the composition (B) may also contain one or more further cosmetic ingredients.

The cosmetic ingredients that may be optionally used in the composition (B) may be any suitable ingredients to impart further beneficial properties to the product. For example, in the composition (A), a solvent, a thickening or film-forming polymer, a surface-active compound from the group of nonionic, cationic, anionic or zwitterionic/amphoteric surfactants, the coloring compounds from the group of pigments, the direct dyes, oxidation dye precursors, fatty components from the group of $C_8$-$C_{30}$ fatty alcohols, hydrocarbon compounds, fatty acid esters, acids and bases belonging to the group of pH regulators, perfumes, preservatives, plant extracts and protein hydrolysates.

The selection of these other substances will be made by the specialist according to the desired properties of the agents. Regarding other optional components and the quantities of these components used, explicit reference is made to the relevant manuals known to the specialist.

Application of the Compositions (A) and (B)

The process as contemplated herein includes the application of both compositions (A) and (B) to the keratinous material. The two compositions (A) and (B) are two different compositions.

As described previously, it is particularly preferred if the composition (A) is first applied to the keratin material, and subsequently the composition (B) is applied to the keratin material in the form of an aftertreatment agent.

In the context of a further embodiment, particularly preferred is a method as contemplated herein including the following steps:
(1) Application of the first composition (A) to the keratin material,
(2) Allowing the composition (A) to act on the keratin material for a period of 1 to 10 minutes, preferably 1 to 5 minutes,
(3) Rinsing the composition (A) out of the keratin material, (4) Application of composition (B) to the keratin material,
(5) Allowing the composition (B) to act on the keratin material for a period of about 1 to about 10 minutes, preferably about 1 to about 5 minutes,
(6) Rinsing the composition (B) out of the keratin material.

The rinsing of the keratinous material with water in steps (3) and (6) of the process is understood as contemplated herein to mean that only water is used for the rinsing process, without the use of other compositions different from compositions (a) and (b).

In a step (1), the composition (A) is first applied to the keratin materials, especially human hair.

After application, the composition (A) is allowed to act on the keratin materials. In this context, application times from 10 seconds to 10 minutes, preferably from 20 seconds to 5 minutes and especially preferably from 30 seconds to 2 minutes on the hair have proven to be particularly beneficial.

In a preferred embodiment of the process as contemplated herein, the composition (A) can now be rinsed from the keratin materials before the composition (B) is applied to the hair in the subsequent step.

In step (4), the composition (B) is now applied to the keratin materials. After application, the composition (B) is now left to act on the hair.

The process as contemplated herein allows the production of dyeings with particularly good intensity and wash fastness even with short exposure times of the compositions (A) and (B). Application times from about 10 seconds to about 10 minutes, preferably from about 20 seconds to about 5 minutes and most preferably from about 30 seconds to about 3 minutes on the hair have proven to be particularly beneficial.

In step (6), the composition (B) is now rinsed out of the keratin material with water.

In the context of a further embodiment, particularly preferred is a method as contemplated herein including the following steps in the order indicated:
(1) Application of the first composition (A) to the keratin material,
(2) Allowing the composition (A) to act on the keratin material for a period of about 1 to about 10 minutes, preferably about 1 to about 5 minutes,
(3) Rinsing the composition (A) out of the keratin material,
(4) Application of composition (B) to the keratin material,
(5) Allowing the composition (B) to act on the keratin material for a period of about 1 to about 10 minutes, preferably about 1 to about 5 minutes,
(6) Rinsing the composition (B) out of the keratin material.

The components required, for the dyeing process, are provided in the form of a multi-component packaging unit (kit-of-parts).

A second object of the present disclosure is a multi-component packaging unit (kit-of-parts) for dyeing keratinous material, including separately prepared
a first container including a first composition (A) and
a second container including a second composition (B), wherein
wherein the compositions (A) and (B) have already been disclosed in detail in the description of the first subject matter of the present disclosure.

Furthermore, the multi-component packaging unit as contemplated herein may also include a third packaging unit including a cosmetic composition (C). The composition (C) includes, as described above, very particularly preferably at least one color-imparting compound.

In a very particularly preferred embodiment, the multi-component packaging unit (kit-of-parts) as contemplated herein includes, separately assembled from one another
a third container including a third composition (C), wherein the third composition (C) has already been disclosed in detail in the description of the first subject matter of the present disclosure.

With respect to the other preferred embodiments of the multi-component packaging unit as contemplated herein, the same applies mutatis mutandis to the procedure as contemplated herein.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process of dyeing keratinous material comprising:
treating the keratinous material with
a first composition (A) comprising:
(A1) one or more organic $C_1$-$C_6$ alkoxy silanes and/or condensation products thereof, and
(A2) at least one colorant compound selected from the group consisting of pigments and direct dyes, and
a second composition (B) comprising:
(B1) at least one alkalizing agent.

2. The process according to claim 1, characterized in that the first composition (A) comprises one or more organic $C_1$-$C_6$ alkoxy silanes (A1) of the formula (S-I) and/or (S-II), $$R_1R_2N-L-Si(OR_3)_a(R_4)_b \qquad (S\text{-}I)$$

where
$R_1$, $R_2$ independently represent a hydrogen atom or a $C_1$-$C_6$ alkyl group,
L is a linear or branched divalent $C_1$-$C_{20}$ alkylene group,
$R_3$, $R_4$ independently of one another represent a $C_1$-$C_6$ alkyl group,
a, stands for an integer from 1 to 3, and
b stands for the integer 3-a, and $$(R_5O)_c(R_6)_d Si-(A)_e-[NR_7-(A')]_f-[O-(A'')]_g-[NR_8-(A''')]_h-Si(R_6')_{d'}(OR_5')_{c'} \qquad (S\text{-}II),$$

where
R5, R5', R5", R6, R6' and R6" independently represent a $C_1$-$C_6$ alkyl group,
A, A', A", A''' and A'' '' independently represent a linear or branched divalent $C_1$-$C_{20}$ alkylene group,
$R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (S-III), $$(A'''')-Si(R_6'')_{d''}(OR_5'')_{c''} \qquad (S\text{-}III),$$

c, stands for an integer from 1 to 3,
d stands for the integer 3-c,
c' stands for an integer from 1 to 3, d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
provided that at least one of e, f, g and h is different from 0, and/or their condensation products.

3. The process according to claim 1, characterized in that the first composition (A) comprises at least one $C_1$-$C_6$ organic alkoxysilane (A1) of formula (S-1) selected from the group consisting of
(3 aminopropyl)triethoxysilane
(3 aminopropyl)trimethoxysilane
(2 aminoethyl)triethoxysilane
(2 aminoethyl)trimethoxysilane
(3 dimethylaminopropyl)triethoxysilane
(3 dimethylaminopropyl)trimethoxysilane
(2 dimethylaminoethyl)triethoxysilane,
(2 dimethylaminoethyl)trimethoxysilane, and condensation products thereof.

4. The process according to claim 1, characterized in that the first composition (A) comprises one or more organic $C_1$-$C_6$ alkoxy silanes (A1) of formula (S-IV), $$R_9Si(OR_{10})_k(R_{11})_m \qquad \text{(S-IV)},$$

where
$R_9$ represents a $C_1$-$C_{12}$ alkyl group,
$R_{10}$ represents a $C_1$-$C_6$ alkyl group,
$R_{11}$ represents a $C_1$-$C_6$ alkyl group,
k is an integer from 1 to 3, and
m stands for the integer 3-k,
and condensation products thereof.

5. The process according to claim 1, characterized in that the first composition (A) comprises at least one $C_1$-$C_6$ organic alkoxysilane (A1) of formula (S-IV) selected from the group consisting of
methyltrimethoxysilane
methyltriethoxysilane
ethyltrimethoxysilane
ethyltriethoxysilane
hexyltrimethoxysilane
hexyltriethoxysilane
octyltrimethoxysilane
octyltriethoxysilane
dodecyltrimethoxysilane,
dodecyltriethoxysilane,
and condensation products thereof.

6. The process according to claim 1, characterized in that the first composition (A) comprises at least one inorganic pigment (A2) selected from the group consisting of colored metal oxides, metal hydroxides, metal oxide hydrates, silicates, metal sulfides, complex metal cyanides, metal sulfates, bronze pigments, mica- or mica-based colored pigments coated with at least one metal oxide, and metal oxychlorides.

7. The process according to claim 1, characterized in that the first composition (A) comprises at least one organic pigment (A2) selected from the group consisting of carmine, quinacridone, phthalocyanine, sorghum, blue pigments having the color index numbers Cl 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and CI 75470.

8. The process according to claim 1, characterized in that the first composition (A) comprises at least one colored pigment (A2) selected from the group consisting of pigments based on a lamellar substrate platelet, pigments based on a lenticular substrate platelet, and pigments based on a substrate platelet comprising a vacuum-metallized pigment.

9. The process according to claim 1, characterized in that the first composition (A) comprises at least one cosmetic ingredient selected from the group consisting of hexamethyldisiloxane, octamethyltrisiloxane, decamethyltetrasiloxane, hexamethylcyclotrisiloxane, octamethylcyclotetrasiloxane, and decamethylcyclopentasiloxane.

10. The process according to claim 1, characterized in that the second composition (B) comprises at least one alkalizing agent (B1) selected from the group consisting of ammonia, $C_2$-$C_6$ alkanolamines, basic amino acids, alkali metal hydroxides, alkaline earth metal hydroxides, alkali metal silicates, alkali metal metasilicates, alkaline earth metal silicates, alkaline earth metal metasilicates, alkali metal carbonates, and alkaline earth metal carbonates.

11. The process according to claim 1, characterized in that the second composition (B) comprises at least one alkalizing agent (B1) selected from the group consisting of ammonia, 2-aminoethan-l-ol, 3-aminopropan-1-ol, 4-aminobutan-l-ol, 5-aminopentan-l-ol, 1-aminopropan-2-ol, 1-aminobutan-2-ol, 1-aminopentan-2-ol, 1-aminopentan-3-ol, 1- aminopentan-4-ol, 3-amino-2-methylpropan-l-ol, 1-amino-2-methylpropan-2-ol, 3- aminopropane-1,2-diol, 2-amino-2-methylpropane-1,3-diol, arginine, lysine, ornithine, histidine, sodium hydroxide,. and potassium hydroxide.

12. The process according claim 1, characterized in that the second composition (B) contains—based on the total weight of the composition (B)—5.0 to 99.0% by weight of water.

13. The process according to claim 1, characterized in that the second composition (B) has a pH of from 7.0 to 12.0.

14. The process according to claim 1, characterized in that the second composition (B) comprises at least one film-forming polymer selected from the group consisting of homopolymers or copolymers of acrylic acid, methacrylic acid, acrylic acid esters, methacrylic acid esters, acrylic acid amides, methacrylic acid amides, vinylpyrrolidone, vinyl alcohol, vinyl acetate, ethylene, propylene, styrene, polyurethanes, polyesters, and polyamides.

15. The process according to claim 1, comprising the following steps:
(1) applying the first agent (A) to the keratin material,
(2) allowing the agent (A) to act on the keratin material for a period of 1 to 10 minutes,
(3) rinsing the agent (A) out of the keratin material,
(4) applying the agent (B) to the keratin material,
(5) allowing the agent (B) to act on the keratin material for a period of 1 to 10 minutes,
(6) rinsing the agent (B) out of the keratin material.

16. Multicomponent packaging unit (kit-of-parts) dyeing of keratinous material, comprising separately prepared
a first container comprising a first composition (A) and
a second container comprising a second composition (B),
wherein the compositions (A) and (B) are defined in claim 1.

* * * * *

UNITED STATES PATENT AND TRADEMARK OFFICE
CERTIFICATE OF CORRECTION

PATENT NO. : 11,826,586 B2
APPLICATION NO. : 17/631829
DATED : November 28, 2023
INVENTOR(S) : Phillip Jaiser et al.

It is certified that error appears in the above-identified patent and that said Letters Patent is hereby corrected as shown below:

In the Specification

Column 4, Line 14 change "R'''" to --R'''--.
Column 5, Line 15 change "$(A)_c$" to --$(A)_e$--.
Column 6, Line 21 change "$(R_4)_b$ (S-I)" to --$(R_4)_b$ (S-I)--.
Column 7, Line 46 change "(3-Dimethylaminopropyl)trimethoxysilane" to --(3-Dimethylaminopropyl)triethoxysilane--.
Column 8, Line 42 change "$(A)_c$" to --$(A)_e$--.
Column 8, Line 49 change "$(A)_c$" to --$(A)_e$--.
Column 8, Line 50 change "$[NR_8 - (A'')]_h$" to --$[NR_8 - (A''')]_h$--.
Column 9, Line 10 change "$(A)_c$" to --$(A)_e$--.
Column 9, Line 22 change "$(A)_c$" to --$(A)_e$--.
Column 9, Line 27 change "$(A)_c$" to --$(A)_e$--.
Column 9, Line 44 change "A''' " to --A''''--.
Column 9, Line 46 change "A''' " to --A''''--.
Column 9, Line 49 change "A''' " to --A''''--.
Column 9, Line 54 change "A''' " to --A''''--.
Column 9, Line 55 change "A''' " to --A''''--.
Column 9, Line 60 change "A''' " to --A''''--.
Column 10, Line 5 change "$Si(R_6'')_a$" to --$Si(R_6'')_d$--.
Column 10, Line 20 change "$(A)_c$" to --$(A)_e$--.
Column 12, Line 28 change "(triethoxysilyl1)propyl1]" to --(triethoxysilyl)propyl]--.
Column 13, Line 56 change "$R_1$" to --$R_{11}$--.
Column 13, Line 64 change "$(R_{10})_m$" to --$(R_{11})_m$--.
Column 14, Line 1 change "$R_1$" to --$R_{11}$--.
Column 14, Line 21 change "$R_1$" to --$R_{11}$--.
Column 29, Line 1 change "(-COO-, -SO$_3$" to --(-COO$^-$, -SO$_3^-$--.
Column 29, Line 53 change "$n^{o0}$" to --$n^o$--.
Column 29, Line 57 change "$n^{o0}$" to --$n^o$--.

Signed and Sealed this
Twenty-fifth Day of February, 2025

Coke Morgan Stewart
*Acting Director of the United States Patent and Trademark Office*

CERTIFICATE OF CORRECTION (continued)
U.S. Pat. No. 11,826,586 B2

Column 30, Line 2 change "$n^{o0}$" to --$n^o$--.
Column 35, Line 60 change "107" to --$10^7$--.
Column 35, Line 60 change "106" to --$10^6$--.
Column 35, Line 61 change "105" to --$10^5$--.
Column 41, Line 35 change "Poly acryldimethyltauramides" to --Polyacryldimethyltauramides--.
Column 44, Line 52 change "$(A)_c$" to --$(A)_e$--.